US012692217B2

(12) United States Patent
Ingram et al.

(10) Patent No.: US 12,692,217 B2
(45) Date of Patent: Jul. 28, 2026

(54) CO-PRODUCTION OF MONOMERS, INCLUDING AT LEAST ONE BIO-BASED MONOMER

(71) Applicant: Archer Daniels Midland Company, Decatur, IL (US)

(72) Inventors: Andrew Ingram, Champaign, IL (US); Erik Hagberg, Decatur, IL (US); Chi-Cheng Ma, Champaign, IL (US); Jessica McClurg, Decatur, IL (US); Kenneth Stensrud, Decatur, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 219 days.

(21) Appl. No.: 17/998,738

(22) PCT Filed: May 12, 2021

(86) PCT No.: PCT/US2021/031969
§ 371 (c)(1),
(2) Date: Nov. 14, 2022

(87) PCT Pub. No.: WO2021/231556
PCT Pub. Date: Nov. 18, 2021

(65) Prior Publication Data
US 2023/0192587 A1    Jun. 22, 2023

Related U.S. Application Data

(60) Provisional application No. 63/025,345, filed on May 15, 2020.

(30) Foreign Application Priority Data

Sep. 15, 2020    (EP) ..................................... 20196216

(51) Int. Cl.
*C07C 51/265*        (2006.01)
*C07C 51/25*         (2006.01)
(Continued)

(52) U.S. Cl.
CPC ............ *C07C 51/265* (2013.01); *C07C 51/25* (2013.01); *C07C 61/20* (2013.01); *C07C 63/26* (2013.01)

(58) Field of Classification Search
None
See application file for complete search history.

(56) References Cited

U.S. PATENT DOCUMENTS 7,385,081 B1    6/2008    Gong
8,242,292 B2    8/2012    Yutaka et al.
(Continued)

FOREIGN PATENT DOCUMENTS

JP      2011-084540 A    4/2011
WO      2016168233       10/2016

OTHER PUBLICATIONS

European Search Report for Application No. EP 20196216, dated Feb. 2, 2021 (Feb. 2, 2021), two pages.

*Primary Examiner* — Sudhakar Katakam
*Assistant Examiner* — Jennifer C Sawyer
(74) *Attorney, Agent, or Firm* — Andrew F. Nilles

(57) ABSTRACT

Processes for the oxidation of carbohydrate dehydration products, such as furanics that can be oxidized to the bio-based monomer 2,5-furandicarboxylic acid (FDCA), are disclosed, according to which certain co-feeds, having been discovered to impart a beneficial reaction stabilizing effect, are oxidized together with the carbohydrate dehydration products. This can advantageously counteract, in whole or in part, detrimental effects of human impurities present in oxidation feed, with such impurities having been generated (Continued)

as byproducts of the upstream dehydrating step. An important co-feed is para-xylene that can be co-oxidized to form the petroleum-based monomer terephthalic acid (TPA), such that co-processing can beneficially yield two valuable monomers, while improving performance, particularly in terms of reaction stability, over comparable processes in which only the first monomer is produced. Related aspects involve opportunities for retrofitting existing monomer production facilities to enable co-processing of carbohydrate dehydration products that can lead to the above-noted advantages.

10 Claims, 5 Drawing Sheets

(51) Int. Cl.
  *C07C 61/20*   (2006.01)
  *C07C 63/26*   (2006.01)

(56)      References Cited

U.S. PATENT DOCUMENTS

| | | | |
|---|---|---|---|
| 2009/0124829 A1 | 5/2009 | Gong | |
| 2013/0171397 A1 | 7/2013 | Ghosh et al. | |
| 2014/0100386 A1 | 4/2014 | Bhattacharyya | |
| 2017/0217917 A1* | 8/2017 | Sanborn | C07D 307/68 |
| 2018/0093961 A1 | 4/2018 | Howard et al. | |
| 2019/0337914 A1 | 11/2019 | Parker et al. | |

* cited by examiner

| Catalyst 1 | mol% | Catalyst 2 | mol% | Catalyst 3 | mol% | Additive | mol% | Solvent | FDCA Confirmed? | TPA Confirmed? |
|---|---|---|---|---|---|---|---|---|---|---|
| Co(OAc)₂ | 1% | NHPI | 10% | | | | | Acetic Acid | | Confirmed |
| Mn(OAc)₂ | 1% | NHPI | 10% | | | | | Acetic Acid | Confirmed | Confirmed |
| Cu(OAc)₂ | 1% | NHPI | 10% | | | | | Acetic Acid | | Confirmed |
| FeCl₃ | 1% | NHPI | 10% | | | | | Acetic Acid | | Confirmed |
| Co(OAc)₂ | 1% | | | | | | | Acetic Acid | | |
| Mn(OAc)₂ | 1% | | | | | | | Acetic Acid | | |
| Cu(OAc)₂ | 1% | | | | | | | Acetic Acid | | |
| FeCl₃ | 1% | | | | | | | Acetic Acid | | |
| V(O)(acac) | 1% | | | | | | | Acetic Acid | | |
| Co(OAc)₂ | 5% | Mn(OAc)₂ | 1% | | | | | Acetic Acid | | Confirmed |
| V(O)(acac) | 1% | NHPI | 10% | | | | | Acetonitrile | | Confirmed |
| Co(OAc)₂ | 1% | NHPI | 10% | | | | | Acetonitrile | | Confirmed |
| Mn(OAc)₂ | 1% | NHPI | 10% | | | | | Acetonitrile | Confirmed | Confirmed |
| Cu(OAc)₂ | 1% | NHPI | 10% | | | | | Acetonitrile | Confirmed | Confirmed |
| FeCl₃ | 1% | NHPI | 10% | | | | | Acetonitrile | Confirmed | Confirmed |
| Co(OAc)₂ | 5% | Mn(OAc)₂ | 1% | HBr | 3% | | | Acetonitrile | Confirmed | Confirmed |
| Co(OAc)₂ | 5% | Mn(OAc)₂ | 1% | HBr | 3% | | | Acetic Acid | Confirmed | Confirmed |
| Co(OAc)₂ | 5% | Mn(OAc)₂ | 1% | HBr | 3% | | | Acetic Acid + 10% Water | Confirmed | Confirmed |
| Co(OAc)₂ | 5% | Mn(OAc)₂ | 1% | HBr | 3% | | | Propanoic acid | Confirmed | Confirmed |
| NHPI | 10% | | | | | | | Acetonitrile | Confirmed | Confirmed |
| NHPI | 10% | | | | | acetaldehyde | 5% | Acetonitrile | | Confirmed |
| Co(OAc)₂ | 5% | Mn(OAc)₂ | 1% | HBr | 3% | acetaldehyde | 5% | Acetic Acid | Confirmed | Confirmed |
| Co(OAc)₂ | 5% | Mn(OAc)₂ | 1% | HBr | 3% | H₂OXYGEN | 5% | Acetic Acid | Confirmed | Confirmed |
| NHPI | 10% | H₂OXYGEN | 5% | | | | | Acetic Acid + 10% Water | Confirmed | Confirmed |
| NHPI | 10% | | | | | | | Acetic Acid + 10% Water | Confirmed | Confirmed |
| NHPI | 10% | | | | | | | Acetonitrile + 10% Water | | Confirmed |
| None | | | | | | | | Acetic Acid | | |
| None | | | | | | | | Acetonitrile | | |
| None | | | | | | | | Acetic Acid + 10% Water | | |
| None | | | | | | | | Propanoic acid | | |
| None | | | | | | | | Water | | |

FIG. 4. Co-Oxidation of P-Xylene and HMF with Various Catalyst Systems

| Catalyst 1 (JM catalog number or provider) | Loading (gm/gm feed) | Catalyst 2 | mol% | Additive | mol% | Solvent ID | FDCA Confirmed? | TPA Confirmed? |
|---|---|---|---|---|---|---|---|---|
| Ru/C (5R619) | 5 wt% | | | NaOH | 240% | Water | Confirmed | Confirmed |
| Pd/C (A102023-5) | 5 wt% | | | NaOH | 240% | Water | Confirmed | Confirmed |
| Pt/C (B501018-5) | 5 wt% | | | NaOH | 240% | Water | Confirmed | |
| Au/TiO (STREM) | 5 wt% | | | NaOH | 240% | Water | Confirmed | |
| Ru/C (5R619) | 5 wt% | NHPI | 10% | NaOH | 240% | Water | Confirmed | Confirmed |
| Pd/C (A102023-5) | 5 wt% | NHPI | 10% | NaOH | 240% | Water | Confirmed | Confirmed |
| Pt/C (B501018-5) | 5 wt% | NHPI | 10% | NaOH | 240% | Water | Confirmed | |
| Au/TiO (STREM) | 5 wt% | NHPI | 10% | NaOH | 240% | Water | Confirmed | |
| Ru/C (5R619) | 5 wt% | | | | | Acetic acid | Confirmed | |
| Pd/C (A102023-5) | 5 wt% | | | | | Acetic acid | | Confirmed |
| Pt/C (B501018-5) | 5 wt% | | | | | Acetic acid | Confirmed | |
| Au/TiO (STREM) | 5 wt% | | | | | Acetic acid | | |
| Ru/C (5R619) | 5 wt% | NHPI | 10% | | | Acetic acid | Confirmed | Confirmed |
| Pd/C (A102023-5) | 5 wt% | NHPI | 10% | | | Acetic acid | | Confirmed |
| Pt/C (B501018-5) | 5 wt% | NHPI | 10% | | | Acetic acid | Confirmed | Confirmed |
| Au/TiO (STREM) | 5 wt% | NHPI | 10% | | | Acetic acid | | Confirmed |
| None | | | | | | Water | | |

FIG. 5. Co-Oxidation with Various Heterogeneous Catalysts

CO-PRODUCTION OF MONOMERS, INCLUDING AT LEAST ONE BIO-BASED MONOMER

CROSS-REFERENCE TO RELATED APPLICATIONS

This application is a national stage entry of International Application No. PCT/US21/031969, filed May 12, 2021, which itself claims priority to U.S. Provisional Patent Application No. 63/025,345, filed May 15, 2020, each of the contents of the entirety of which are incorporated by this reference.

FIELD OF THE INVENTION

The present invention relates, from one perspective to processes for making terephthalic acid (TPA) and to the polymers that can be made therefrom. From another perspective, the present invention relates to processes for making TPA's biobased analog 2,5-furandicarboxylic acid (FDCA) and to the polymers that can be made therefrom.

BACKGROUND OF THE INVENTION

The depletion of fossil fuels has created major incentives for seeking alternative sources to petroleum-based carbon for the synthesis of so-called "platform" molecules that can serve as the building blocks for commercially significant products. Biomass is currently viewed as a potential replacement from which many such high value chemicals can be derived, but the development of sustainable technologies for the production of such chemicals from renewable resources remains a significant challenge.

The bio-based monomers, 2,5-furandicarboxylic acid (FDCA) and its dimethyl ester derivative, 2,5-furandicarboxylic acid, dimethyl ester (FDME) are recognized as important starting materials in the production of poly(alkylene furan dicarboxylate) polymers that can substitute for their known, mass-produced petroleum derived analogs, namely poly(alkylene terephthalate) polymers, such as polyethylene terephthalate (PET). A prominent example of a poly(alkylene furan dicarboxylate) polymers is poly(ethylene furan dicarboxylate), or PEF, obtained by reaction of FDCA or FDME with ethylene glycol. The bio-based polymer (bio-plastic) PEF exhibits superior properties in a number of respects, relative to its petroleum derived analog PET, particularly in the area of packaging. For example, blends of PEF and PET can provide improved barrier properties with respect to carbon dioxide and oxygen, prolonging shelf life over that obtained with pure PET and providing an acceptable container for products such as beer that are susceptible to oxidative degradation. Other packaging applications of PEF include films used to manufacture pouches, wrappers, and heat shrink materials having high mechanical strength and recyclability.

In general, both FDCA and FDME are useful platform molecules in the production of polyamides, polyurethanes, and polyesters having diverse applications as plastics, fibers, coatings, adhesives, personal care products, and lubricants. The commercial significance of these molecules is evidenced, for example, in a 2004 study by the U.S. Department of Energy, identifying FDCA as one of twelve priority chemicals for establishing the "green" chemical industry of the future. Due to its structural similarity to terephthalic acid (TPA), the potential of FDCA as a substitute monomer for synthesizing polyesters has been recognized at least as early as 1946, for example in GB621971A, and a number of parties have invested significant effort over a number of years toward achieving a commercially viable process to manufacture FDCA. In terms of FDCA synthesis from bio-based starting materials, advancements are described in U.S. Pat. No. 10,538,499, according to which a feed comprising a six-carbon sugar unit (e.g., fructose) is subjected to integrated processing steps, the first of which is a dehydrating step to provide 5-hydroxymethylfurfural (HMF) or certain derivatives, such as its ester or ether derivatives. The dehydration product is then oxidized to the desired FDCA, according to a similar Mid-Century type oxidation as employed for the oxidation of p-xylene to make TPA, using a homogeneous catalyst system including cobalt, manganese and bromine components. Despite these extensive efforts, the commercial production of FDCA has not yet been realized and improvements in bio-based synthesis routes to FDCA and its derivatives are continually being sought, in an effort to establish economic viability on the commercial scale.

SUMMARY

Certain aspects of the invention relate to the discovery of methods for ameliorating or even eliminating detrimental effects associated with the presence of at least certain species of humins, which are highly colored and generally water-insoluble byproducts of the dehydration of carbohydrates, in processes utilizing such carbohydrates as starting materials in the bio-based synthesis of FDCA and derivatives thereof.

For example, at least certain species of humins produced in the acid-catalyzed dehydration of carbohydrates having a six-carbon sugar unit (e.g., hexose sugars and their oligomers and polymers) tend to consume, or limit the useful capacity of, homogeneous Mid-Century oxidation catalysts. These catalysts have been the most commonly proposed for oxidizing 5-hydroxymethylfurfural (HMF) and/or its derivatives (e.g., ester and/or ether derivatives) that are formed in the upstream dehydration.

More generally, it has been determined that, when these humins as produced in a preceding dehydration step are present in the oxidation feed together with HMF and/or its derivatives, operating parameters can become constrained in relation to the use of both homogeneous and heterogeneous catalysts. In a homogeneous catalyzed oxidation, this may manifest in (i) the need for increased catalyst concentration to maintain desired conversion and yield profiles, and (ii) a narrower "operating window" or set of conditions (temperature, pressure, time on stream) under which favorable performance is achieved, prior to loss of reaction or "light off" (e.g., based on a determination of oxygen consumption). In the heterogeneous catalyzed oxidations that have from time to time been proposed for oxidizing HMF and/or its derivatives to provide FDCA, these humins are problematic, too, in that they can lead to catalyst deactivation as a result of their deposition on the solid catalyst particles.

In the face of these and other disadvantages associated with the oxidation of carbohydrate dehydration products having at least certain species of humins included therein, it has now been discovered that certain co-feeds surprisingly impart a beneficial stabilizing effect (e.g., a reaction stabilizing effect) that counteracts the operating constraints noted above. This can result in a partial or complete restoration of the useful or economically favorable operating window, which is otherwise constrained by the presence of these humins. The stabilizing effect can be evidenced by a broader range of possible operating conditions, including lower bounds of catalyst concentration, temperature, and/or oxygen partial pressure, as needed to attain favorable activity, selectivity, and/or stability (time on stream over which a desired level of performance is maintained). Importantly, such co-feeds can be oxidized to form other valuable monomers, in an analogous manner to the oxidation of HMF and/or its derivatives to FDCA. Advantageously, oxidation of both such stabilizing co-feeds and HMF can occur under the same conditions and therefore utilize the same reactor and catalyst system, whether homogeneous or heterogeneous. A particular co-feed of interest is para-xylene, often obtained as a product of crude oil refining, which can be oxidized to terephthalic acid (TPA). Accordingly, certain embodiments are directed to the co-production of monomers through oxidation, such as in the case of co-production of FDCA and TPA.

In the particular co-oxidative context involving the use of Mid-Century-type oxidation catalysts, processes for the co-production of FDCA and TPA comprise co-feeding FDCA-forming furanics and para-xylene to an oxidation reactor containing a homogeneous Mid-Century-type oxidation catalyst and reactant oxygen, such that the FDCA-forming furanics and para-xylene are effectively reacted in the same environment, wherein the para-xylene is employed in a sufficient amount as to impart a stabilizing effect (e.g., improve the performance of the reaction system in terms of its ability to oxidize FDCA-forming furanics in the presence of at least certain species of humin byproducts formed in an upstream acid-catalyzed, especially mineral acid-catalyzed, dehydration of one or more carbohydrates (e.g., fructose) having a 6-carbon sugar unit) as described above. According to representative processes, upstream carbohydrate dehydration is integrated with oxidation of both (i) the dehydration product (e.g., comprising HMF and/or its derivatives) that forms a first monomer and (ii) a stabilizing agent (e.g., para-xylene) that forms a second monomer.

Yet other aspects relate to the use of a co-feed in the oxidation of a carbohydrate dehydration product comprising at least some humins, in which the co-feed partially or completely restores performance (e.g., catalyst activity), relative to a comparative (or baseline) process without co-feed but having the same humins removed from or absent in the dehydration product. Advantageously, performance restoration may be realized using only a minor amount of co-feed (e.g., on a molar basis) relative to the carbohydrate dehydration product, based on the portion thereof that is oxidizable to the desired monomer (e.g., "on path" FDCA-forming furanics).

Apart from the particular beneficial aspects provided by a co-oxidation method of the present invention in relation to the impact of humins in a carbohydrate dehydration product from which FDCA is to be made by oxidation, those of skill in the polyesters art area will appreciate other benefits provided by such a co-oxidation process in the utilization of existing, commercial processes or associated equipment used in the production of monomers through oxidation and/or their corresponding polymers (e.g., polyesters such as PET), by the integration of such processes or equipment with a carbohydrate dehydration step or associated elements, including a dehydration reactor. Advantageously, such retrofitting can allow for the co-production and co-processing of both conventional and biobased monomers with investing only a fraction of the capital and time otherwise needed for construction of a new standalone ("greenfields") bio-based polyester production facility. A specific type of retrofit may involve, for example, the grafting of a fructose dehydration reactor and associated equipment onto an underutilized or temporarily decommissioned TPA production plant. This can allow for the co-feeding of HMF and/or its derivatives (e.g., ester or ether derivatives, depending on the whether a carboxylic acid solvent or an alcohol solvent is used for forming a solution of the carbohydrate such as fructose that is subjected to dehydration) with para-xylene. Following oxidation of the co-feed, FDCA and TPA may then be provided together in the oxidation product, i.e., as a mixed monomer composition or co-product.

Particular embodiments of the invention having these other benefits in mind are thus directed to processes for making a mixed monomer composition comprising first and second monomers, for example 2,5-furandicarboxylic acid (FDCA), which may be a bio-based monomer, and terephthalic acid (TPA), which may be and conventionally is a petroleum-based monomer, in more particular embodiments taking advantage of the existing technical, physical, and commercial assets and infrastructure associated with producing the latter for the more facile commercial realization of producing the former. The processes comprise contacting an oxidation feed, in the presence of oxygen (e.g., in the presence of an oxygen-containing gas such as air), with an oxidation catalyst to provide the mixed monomer composition. The oxidation feed comprises (i) a dehydration product of one or more carbohydrates (e.g., fructose) having a 6-carbon sugar unit, and (ii) para-xylene.

The capability of oxidizing, in a single reactor under a common set of oxidation conditions, an oxidation feed comprised of both a dehydration product of one or more hexoses and para-xylene to generate a mixed monomer composition would be of significant value in the art both in terms of asset utilization but also in other ways, for example, providing a means for providing both conventional, non-renewable resource-based monomers and renewable resource-based monomers for the same market application in the relative proportions and in the amounts that customers require, without significant delay and especially without the significant capital expense that so often deters new monomer and new polymer development.

We have found in this regard that a number of oxidation catalysts, including both homogeneous and heterogeneous catalysts, are capable of being used in a co-oxidation method according to the present invention to produce a mixed monomer composition including both of FDCA and TPA, in addition to the Mid-Century-type oxidation catalysts that have been used commercially for years for producing TPA (and in turn, the esters of TPA).

In the retrofit context of application just mentioned or in general in relation to realizing the stabilizing benefits mentioned previously, the dehydration and oxidation steps may optionally be combined with a number of additional steps that include color stabilizing, derivatizing (e.g., esterifying), separating, and polymer forming. The polymer forming step may (in relation to the formation of polyesters and copolyesters) itself comprise sub-steps of (i) esterifying or transesterifying, and (ii) polymerizing by polycondensation. These steps and sub-steps may be practiced according to a number of different process configurations, the selection of which would be apparent to one skilled in the art having knowledge of the present disclosure, and in view of the particular feeds being processed and desired end products.

One particular embodiment, for example, may comprise refining the mixed monomer composition into fractions enriched in the different monomers (e.g., and ideally substantially free of the monomers in which they are depleted), such as into a first, FDCA-enriched fraction and a second, TPA-enriched fraction. Either or both of these fractions may then be subjected to color stabilizing, such as by hydrogenation of color-forming aldehyde byproducts (e.g., 5-formyl-2-furancarboxylic acid (FFCA) that may be present in the FDCA enriched fraction and/or 4-carboxybenzaldehyde (4-CBA) that may be present in the TPA-enriched fraction) or other remediation/purification steps prior to use in a downstream polymer forming step. Another particular embodiment may comprise using remediation/purification steps without separation of the mixed monomer composition into fractions, for example by subjecting the entire mixed monomer composition to color stabilizing, such as by hydrogenation of both FFCA and 4-CBA in the same process stream. The resulting, stabilized composition (or mixed monomer composition) may then be separated into a stabilized, first fraction (e.g., a stabilized FDCA-enriched fraction) and a stabilized second fraction (e.g., a stabilized TPA-enriched fraction), with the subsequent use of these fractions in separate polymer forming steps. In this manner, separate copolymers may be produced, such as one having furandicarboxylate moieties and preferably being substantially free of (or at least having less of) benzenedicarboxylate moieties (e.g., in the case of PEF), and another having benzenedicarboxylate (or terephthalate) moieties and preferably being substantially free of (or at least having less of) furandicarboxylate moieties (e.g., in the case of PET). Alternatively, the stabilized composition (e.g., comprising both FDCA and TPA oxidation products) may be used directly (e.g., without separation) in a subsequent polymer forming step, for example, producing a copolyester with one or more alcohols/polyols (e.g., ethylene glycol), such as a copolymer having both furandicarboxylate moieties and benzenedicarboxylate moieties.

Other aspects relate to the further downstream polymerization of one or both of these monomers or of derivatives thereof, for example, of furanoate esters and terephthalate esters for making polyesters, either separately or together. In the former case (polymerization separately), these monomers may be separated as formed from the oxidation, or they may be manipulated to facilitate their separation, for example, by forming convenient derivatives of the monomers (e.g., conveniently the same (ester) derivatives as contemplated for being polymerized) which are more easily or more economically separated by reason of their having lower boiling points and/or a greater relative volatility difference, compared to their underivatized form. For example, the furanoate ester and terephthalate esters should be readily separable by distillation. In the latter case (polymerization together), a resulting copolymer may be produced having, for example, both FDCA-related moieties and TPA-related moieties.

Where the downstream polymerization concerns the formation of one or more homopolyesters or copolyesters from one or more of the monomers or derivatives thereof, either separately or in one or more combinations with each other and optionally other comonomers or oligomers, such FDCA-related related moieties may be furandicarboxylate moieties and such TPA-related moieties may be terephthalate moieties (or benzene dicarboxylate moieties), obtained from polycondensation, following reaction of FDCA and/or TPA, or otherwise ester derivatives of FDCA and/or TPA, with a co-monomer having at least two hydroxyl groups (e.g., a diol).

In yet other embodiments, a downstream polymer forming step may include reacting, as a co-monomer, a hydroxyl (alcohol) derivative of one or both of FDCA and TPA (e.g., a diol derivative of one or both of FDCA and TPA), separately or in combination, with a polyacid or its ester derivative thereof to produce a polyester having one or both of FDCA-related moieties and TPA-related moieties.

Where the downstream polymerization concerns the formation of one or more polyamides or copolyamides from one or more of the monomers or derivatives thereof, either separately or in one or more combinations with each other and optionally other comonomers or oligomers, in certain embodiments one or both of FDCA and TPA, separately or in combination, may be reacted with a co-monomer having at least two amino groups (e.g., a diamine), to produce a polyamide having one or both of FDCA-related moieties and TPA-related moieties.

In further embodiments, a downstream polymer forming step may include reacting, as a co-monomer, a hydroxyl (alcohol) derivative of one or both of FDCA and TPA (e.g., a diol derivative of one or both of FDCA and TPA), separately or in combination, with a polyisocyanate to produce a polyurethane having one or both of FDCA-related moieties and TPA-related moieties.

In further embodiments, a downstream polymer forming step may include reacting, as a co-monomer, an amino derivative of one or both of FDCA and TPA (e.g., a diamino derivative of one or both of FDCA and TPA), separately or in combination, with a polyacid to produce a polyamide having one or both of FDCA-related moieties and TPA-related moieties.

In further embodiments, a downstream polymer forming step may include reacting an acyl derivative of one or both of FDCA and TPA (e.g., a diacyl chloride derivative of one or both of FDCA and TPA), separately or in combination, with a co-monomer having at least two amino groups (e.g., a diamine), to produce a polyamide having one or both of FDCA-related moieties and TPA-related moieties.

In further embodiments, a downstream polymer forming step may include reacting an isocyanate derivative of one or both of FDCA and TPA (e.g., a diisocyanate derivative of one or both of FDCA and TPA), separately or in combination, with a co-monomer having at least two hydroxyl groups (e.g., a diol), to produce a polyurethane having one or both of FDCA-related moieties and TPA-related moieties.

One skilled in the art having knowledge of the present disclosure will appreciate from the above that the co-oxidation of precursors of FDCA and of TPA to produce the commercially desirable monomers FDCA and TPA (and by extension various known derivatives thereof) enables a very substantial number of desirable downstream polymer scenarios to be considered based on one or both of FDCA and TPA, of which the above described embodiments are merely an illustrative portion.

Other embodiments are directed to methods for modifying a TPA production plant comprising an oxidation reactor adapted to receive para-xylene and oxygen (or an oxygen-containing gas) as feeds, as well as a downstream terephthalic acid crystallization and recovery section configured to separate solvent from TPA and recycle it to the oxidation reactor. The methods comprise retrofitting the terephthalic acid production plant with a connection from an existing inlet of the oxidation reactor, or from an added inlet of the oxidation reactor, to an upstream carbohydrate dehydration reactor.

In yet another aspect, the present invention relates to the discovery that the para-xylene can be suitably employed as a co-solvent, e.g., for furanic precursors of FDCA, in an upstream carbohydrate dehydration reactor preliminary to a co-oxidation of both a dehydration product of one or more hexoses and para-xylene to generate a mixed monomer composition where, for example, in the retrofit scenario just given there is a connection made from an inlet of an existing oxidation reactor for converting para-xylene to TPA to such an upstream carbohydrate dehydration reactor. Consequently, in certain embodiments, at least a portion of the para-xylene to be oxidized for providing a corresponding portion of the mixed monomer composition can be introduced via the product mixture from an upstream carbohydrate dehydration reactor alongside one or more FDCA-forming furanics generated therein.

Introducing at least a portion of the para-xylene to be oxidized in this way enables some significant benefits to be realized. For example, where the dehydration utilizes hydrobromic acid in addition to acetic acid and is integrated with a subsequent Mid-Century type oxidation step so that the dehydration product is fed directly into the subsequent oxidation step as described in U.S. Pat. No. 10,538,499, at least a portion of the para-xylene can in fact displace a portion of the substantial quantities of acetic acid that in U.S. Pat. No. 10,538,499 are contemplated as optimally being recovered and recycled following the oxidation step, so that capital and operating expenses associated with this recycle can be reduced. Moreover, the amount of heat energy generated in the co-oxidation step relative to the amount of acetic acid needing to be recycled in an integrated process conducted otherwise in keeping with U.S. Pat. No. 10,538, 499 is significantly increased, enabling the energy costs associated with the recycle acetic acid stream to be at least partially offset. Consequently, in certain embodiments of a process according to the present invention wherein a carbohydrate dehydration step is combined with a subsequent oxidation step to generate a mixed monomers composition comprising both FDCA and terephthalic acid, an amount of para-xylene is fed to the oxidation step from a preceding dehydration step that can be well in excess of that amount that would be indicated for providing a stabilizing effect or benefit as previously described in consideration of what humins are present in the materials to be supplied to the oxidation step—for example, in certain embodiments, up to 20 weight percent of that portion of the feed for generating a mixed monomer composition in a subsequent oxidation step (especially utilizing a Mid-Century type oxidation but optionally using another oxidation catalyst, as exemplified below) that is obtained from a carbohydrate dehydration step may be para-xylene.

All of these and still other aspects, embodiments, and associated advantages will become apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures.

FIG. 4 provides a Table of experimental results associated with the Examples below.

FIG. 5 provides a second Table of experimental results associated with the Examples below.

Figure 1:
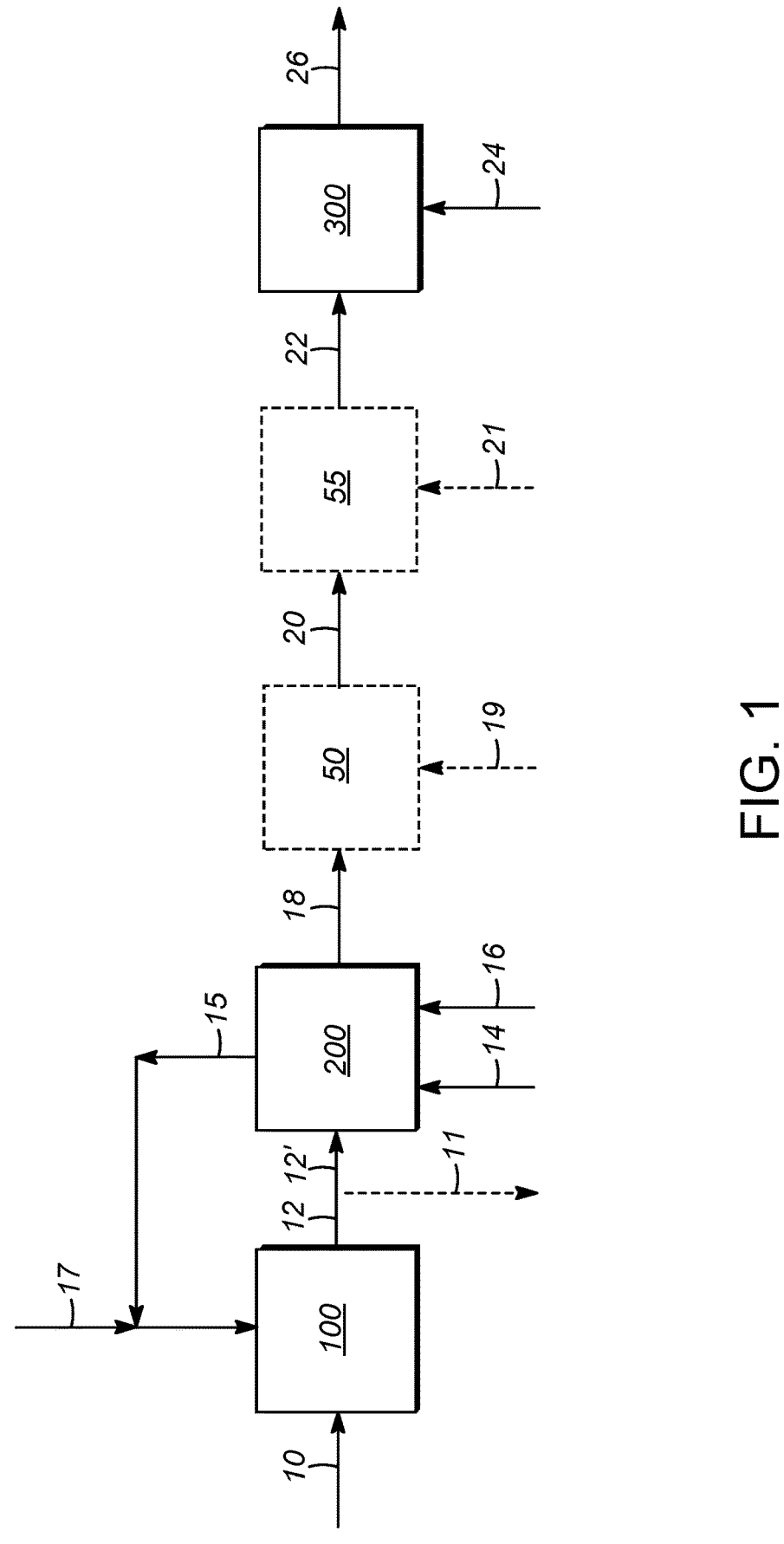
FIG. 1 illustrates a multi-step process for making a copolymer by forming a mixed monomer composition and using this in a polymer forming step.
Figure 2:
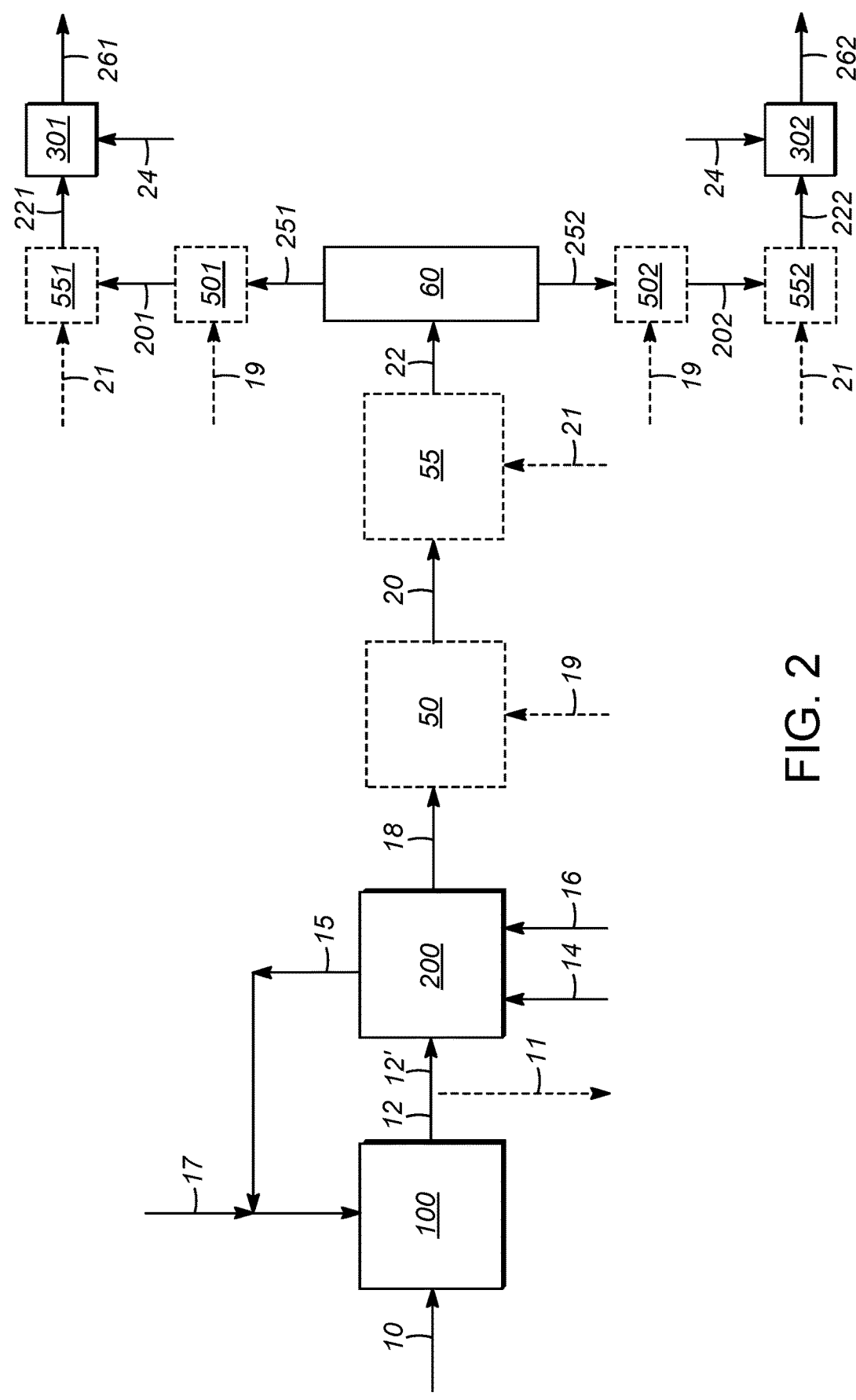
FIG. 2 illustrates a multi-step process according to which the mixed monomer composition is separated into fractions, prior to using one or both fractions in a polymer forming step.
Figure 3:
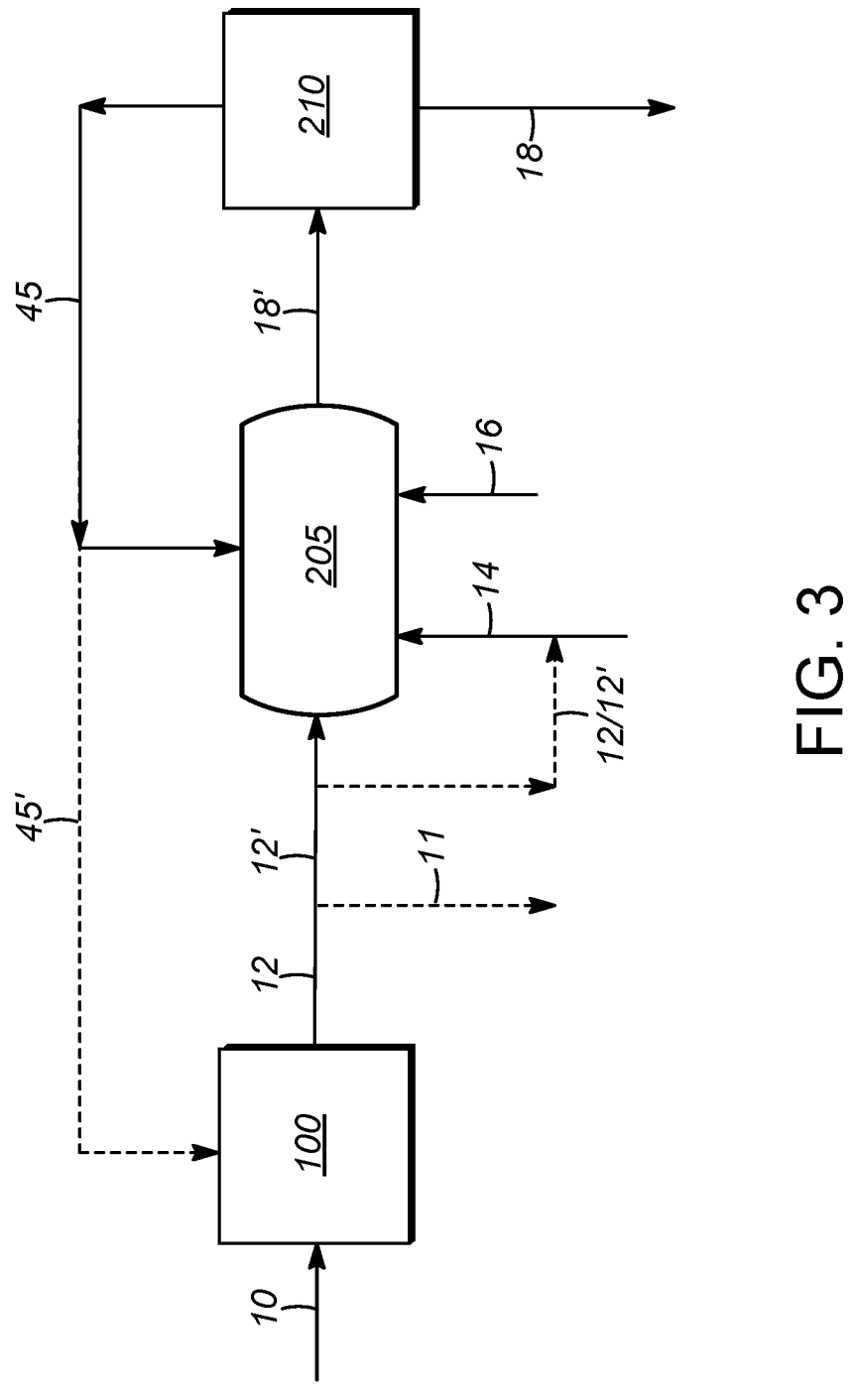
FIG. 3 illustrates the use of a carbohydrate dehydration reactor for modifying a terephthalic acid production plant.

The same reference numbers and other reference characters are used throughout FIGS. 1-3 to represent the same or similar features. These figures should be understood to present simplified overviews of processes and their associated equipment, in order to demonstrate certain principles involved. The depicted elements are not necessarily drawn to scale; nor do the illustrated processes and equipment associated therewith preclude the addition of any upstream, intermediate, or downstream steps, such as separating, combining, and/or reacting steps. For example, an intermediate recycling step could involve both separating and combining. As is readily apparent to one skilled in the art having knowledge of the present disclosure, other processes may have alternative configurations and/or components that are governed by specific operating objectives, but which alternatives are nonetheless within the scope of the invention as defined by the appended claims.

DETAILED DESCRIPTION OF EMBODIMENTS

Certain aspects of the invention relate to processes in which a dehydration product, such as the product of the dehydration of a hexose carbohydrate (e.g., fructose), is subjected to oxidation in the presence of a "co-feed," which may be considered a "stabilizing co-feed" to the extent that it provides or is available to provide oxidation reaction stabilizing benefits as described herein. This co-feed itself may become oxidized to yield a useful product, such as a second monomer that is different from a monomer obtained from oxidation of the dehydration product. Accordingly, such "co-feed" or "stabilizing co-feed" can also be characterized in such cases as a "second monomer-forming co-feed." In any of these designations, the term "co-feed" should not be interpreted to impose any limitation on the amount of its addition or presence relative to that of the dehydration product or any portion thereof, such as the "on path" FDCA-forming furanics portion that is oxidizable to a desired monomer, such as FDCA. Accordingly, particular embodiments described herein are directed to the addition of the co-feed in sub-stoichiometric amounts, or at a molar ratio of less than 1, relative to the moles of FDCA-forming furanics, whereas other embodiments are directed to its addition in excess stoichiometric amounts, or at a molar ratio of greater than 1. The latter case may arise, for example, in the case of retrofitting an existing facility (plant) used for the oxidation of p-xylene to make TPA, in order to accommodate a relatively minor addition of a dehydration product as a source of a bio-derived monomer as might be desired, for example, in the early commercialization of FDCA.

The terms "wt-%" and "wt-ppm," as used herein, are used to designated percentage by weight and parts per million by weight, respectively. The term "mol-%" is used to designate a molar percentage. Unless otherwise indicated, the phrase "being (or is) substantially free of," can mean, in various embodiments, "having (or has) less than 5 wt-% of," "having (or has) less than 3 wt-% of," or "having (or has) less than 1 wt-% of." In the case of references to "byproducts" such a humin byproducts and color-forming byproducts, these may alternatively be referred to as "contaminants" or "impurities".

Processes are described herein for making 2,5-furandicarboxylic acid (FDCA) in combination with other monomers, such as terephthalic acid (TPA). Certain processes expressly include steps of "esterifying" to form ester derivatives of FDCA and TPA, whereby one or preferably both of the carboxylic acid groups of these dicarboxylic acids are instead ester groups, such as alkyl ester groups (in the case of a mono- or dialkyl ester derivative) or aryl ester groups (in the case of a mono- or diaryl ester derivative), with methyl ester groups, ethyl ester groups, or phenyl ester groups being specific examples. In the case of methyl ester groups, the preferred ester derivative of FDCA is 2,5-furandicarboxylic acid, dimethyl ester (FDME) and the corresponding preferred ester derivative of TPA is dimethyl terephthalate (DMT), which can be formed by reaction of FDCA and TPA, respectively, with sufficient quantities of methanol.

Parenthetically, those skilled in the art having knowledge of the present disclosure will appreciate that processes described herein may also be applied in the production of a broad range of other derivatives of FDCA and TPA, including, but not limited to, ester derivatives other than FDME and DMT, in addition to hydroxyl (alcohol) derivatives, which include hydroxyalkyl derivatives; ether derivatives, which include alkoxy derivatives; amino derivatives; acyl derivatives, which include acyl halide derivatives such as acyl chloride derivatives; isocyanate derivatives; aldehyde derivatives; and acetal derivatives. In the case of such derivatives, one or both of the two carboxy-substituted furan ring members of FDCA or one of both of the two carboxy-substituted benzene ring members of TPA may instead be substituted with carboxylic acid groups other than carboxy and/or with these other groups, to provide, for example, the corresponding diol, dialkanol (e.g., dimethanol), diamino, diacyl (e.g., diacyl chloride), diester, diisocyanate, ether-acid, ether-ester, ester-acid, ester-aldehyde, ether-aldehyde, ether-acetal, ester-acetal, acetal-acid, hydroxyl-acid, hydroxyalkyl-acid, hydroxyl-ester, hydroxyalkyl-ester, hydroxyl-acetal, hydroxyalkyl-acetal, hydroxyalkyl-hydroxyalkyl, diacetal and/or aldehyde-acetal derivatives, with the "acid" substitution referring to carboxy or a radical such as carboxymethyl, formed by a carboxylic acid other than acetic acid.

In this regard. as will be explained more fully hereafter, the formation of these various derivatives from the exemplary monomers FDCA and TPA may be desirable in relation to the mixed monomer composition for facilitating a separation of the mixed monomer composition into a fraction enriched in FDCA and preferably substantially completely depleted in TPA on the one hand, and a fraction enriched in TPA and preferably substantially completely depleted in FDCA on the other, and in general, for addressing the tendency of any aldehyde-containing species from the oxidation to undergo aldol condensation and produce color over time in the mixed monomer composition or in the enriched monomer fractions having these aldehyde-containing species. The ester derivatives are particularly appropriate for accomplishing these objectives in the context of producing the homopolyester and copolyester polymers in which TPA and FDCA are expected to be most commonly commercially employed, but those of skill in the polymerization art will certainly be well able to conceive of other derivatives of FDCA and TPA that will be able to be employed in a subsequent polymer forming step and of the relative advantages and disadvantages of these various possible derivatives in the context of making a desired polymer product or combination of polymer products.

In the case of the ester derivatives, like their parent carboxylic acid (e.g., dicarboxylic acid) compounds, these may be used as monomers in polymer forming steps as described herein. Therefore, any such ester derivative may be equivalently referred to as an "ester derivative monomer"; consistent with the preceding paragraph, however, the fact that hereafter we will address and describe predominantly the "ester" derivatives and the "esterification" of the FDCA and TPA diacids should not be taken as implying that other derivatives as just described may not also be used as monomers in subsequent polymer forming steps, but rather as reflecting only the expectation that the co-produced FDCA and TPA will most commonly be destined for application in the manufacture of polyester products. Consequently, any subsequent mention of "ester derivatives" or "esterification" will be understood as including any other form of derivative or derivatization of FDCA and/or TPA, unless those skilled in the art would understand in context that only the ester derivatives or esterification may reasonably be contemplated.

Particular processes disclosed herein are for making a mixed monomer composition comprising FDCA and TPA using an oxidation step in which both of these monomers are formed. The processes may comprise contacting an oxidation feed, in the presence of oxygen (e.g., in an oxygen-containing feed such as air), with an oxidation catalyst to provide the mixed monomer composition. The oxidation feed may comprise (i) a dehydration product of one or more carbohydrates (e.g., fructose) having a 6-carbon sugar unit, and (ii) para-xylene. Component (i) of the oxidation feed may thus comprise FDCA-forming furanics, and representative processes may comprise feeding both components (i) and (ii) to an oxidation reactor containing an oxidation catalyst (e.g., a homogeneous or heterogeneous catalyst) and reactant oxygen.

A carbohydrate having a six-carbon sugar unit means a six-carbon sugar, an oligomer of a six-carbon sugar, or a polymer of a six-carbon sugar. Such carbohydrates include starch, amylose, galactose, cellulose, hemicellulose, inulin, fructan, glucose, fructose, sucrose, maltose, cellobiose, lactose, and sugar oligomers. These carbohydrates may also be referred to as hexose carbohydrates and may be obtained from one or a combination of products, byproducts, or intermediate products of a wet or dry grain milling process, with such products including one or more of fructose syrup, crystalline fructose, high fructose corn syrup, crude fructose, purified fructose, or molasses. A preferred carbohydrate is fructose, which may be provided to the dehydration step in pure or purified form (e.g., at greater than 90% or 95% purity).

FDCA-forming furanics refer to furan ring-containing monomeric and dimeric molecules which form FDCA through catalytic oxidation as described herein. FDCA-forming furanics, along with unwanted byproducts (e.g., humins) may be obtained as the dehydration product, from dehydrating one or more carbohydrates having a six-carbon sugar unit at elevated temperatures and in the presence of an acid catalyst, which may be homogeneous or heterogeneous in nature. FDCA-forming furanics include 5-(hydroxymethyl)furfural (HMF), and, in the case of their formation in the presence of a lower carboxylic acid (i.e. a $C_1$ to $C_6$ aliphatic carboxylic acid, such as acetic acid), can include ester derivatives of HMF, such as 5-(acetoxymethyl)furfural, or, in the case of their formation in the presence of a lower alcohol solvent (i.e. a $C_1$ to $C_6$ aliphatic alcohol; e.g., methanol), can include ether derivatives of HMF, such as 5-(methoxymethyl)furfural. Other FDCA-forming furanics can include derivatives of HMF such as 2,5-diformylfuran, and 5-formyl-2-furancarboxylic acid. FDCA-forming furanics further include the HMF dimer 5,5'-[oxybis(methylene)] di(2-furaldehyde), as well as HMF oligomers. Examples of non-FDCA forming furanics include, but are not limited to, furfural, 2-(hydroxyacetyl)furan, and 2-(acetoxyacetyl) furan. In preferred embodiments, the dehydration product may comprise, such that the FDCA-forming furanics may include, one or more of HMF and/or an ester or ether derivative thereof. In the case of the dehydration being performed using an acetic acid catalyst and solvent, the FDCA-forming furanics may include HMF, 5-(acetoxymethyl)furfural, and HMF dimer. In one embodiment as described more fully hereafter, the dehydration utilizes hydrobromic acid in addition to acetic acid and is integrated with a subsequent Mid-Century type oxidation step so that the dehydration product is fed directly into the subsequent oxidation step consistent with U.S. Pat. No. 10,538,499, except that a stabilizing co-feed is also supplied to the subsequent oxidation step. As used herein throughout, ester derivatives of HMF are to be understood to be compounds which would or do result from the esterification of the hydroxyl group of HMF with a carboxylic acid via condensation reaction, e.g. the condensation of acetic acid and the hydroxyl group of HMF to furnish 5-(acetoxymethyl)furfural. As used herein throughout, ether derivatives of HMF are to be understood to be compounds which would or do result from the etherification of the hydroxyl group of HMF, e.g. the etherification of the hydroxyl group of HMF under methylating conditions to furnish 5-(methoxymethyl)furfural.

According to processes in which an oxidation feed comprises a dehydration product, such as a product including FDCA-forming furanics, at least two processing steps may be performed, namely the steps of (i) dehydrating the carbohydrate having a six-carbon sugar unit to provide a dehydration product comprising FDCA-forming furanics, and (ii) oxidizing the dehydration product, in an oxidation feed further comprising para-xylene, to provide FDCA, together with TPA. Such steps may be integrated as described above, providing advantages that may include the use of the same acetic acid (or acetic acid and water) solvent in both steps. Furthermore, the use of a common solvent, in addition to the suitability of hydrobromic acid for use as a further acid catalyst for the dehydration step, provides the added advantage that acetic acid and optionally at least a portion of the bromine source for the Mid-Century oxidation step (in the form of hydrobromic acid, typically), can be recycled (and preferably substantially completely recycled) from the oxidizing step back to the dehydrating step. This results in significant capital and operating cost reduction associated with converting a carbohydrate having a six-carbon sugar unit to FDCA. Furthermore, the integrated process is amenable to being fabricated by retrofitting existing equipment used in such oxidations, for example, in the oxidation of p-xylene to make TPA.

The oxidizing step may be performed by adding a co-feed such as para-xylene that imparts or is available to impart a reaction stabilizing effect as described above, the latter scenario being contemplated where a dehydration product is not fed directly and without any intervening further processing to the oxidizing step, such intervening processing, for example, being in the way of refining or purification to remove humins from the dehydration product as a whole or in the form of some kind of pretreatment of humins in the dehydration product to mitigate or at least partly mitigate the detrimental effects of at least those same species of humins therein addressed by the reaction stabilizing effect of the co-feed.

Beneficially, this reaction stabilizing effect can be realized with a relatively minor amount of the co-feed (if appropriate and desired, given a manufacturer's desired product mix in a mixed monomer composition comprising both FDCA and a second monomer such as TPA), which providentially also serves as a source of a second monomer. In some embodiments, the reaction stabilizing effect may be realized with adding the co-feed (e.g., batchwise or continuously to an oxidation reactor) in an amount representing less than 50 mol-%, based on the number of moles (e.g., based on the total number of moles of HMF, 5-(acetoxymethyl)furfural, and HMF dimer) of FDCA-forming furanics being oxidized. For example, the co-feed may be added in a sub-stoichiometric (sub-molar) amount representing less than 45 mol-% (e.g., from 5 mol-% to 45 mol-%) of the FDCA-forming furanics. In other embodiments, the co-feed (e.g., para-xylene) may be added in a sub-stoichiometric amount representing less than 80 mol-% (e.g., from 10 mol-% to 80 mol-% or from 30 mol-% to 60 mol-%), of the FDCA-forming furanics.

However as already mentioned above, in still other embodiments, a greater amount, such as a stoichiometric equivalent (molar equivalent) amount, or excess stoichiometric (excess molar) amount, of the co-feed may be desirably added, for example, to produce a second monomer in a greater proportion to the first monomer as well as provide the reaction stabilizing effect for the production of the first monomer, and the process of the present invention possesses the operational flexibility to accommodate this scenario as well.

For example, the co-feed may be added in an amount representing greater than 85 mol-% (e.g., from 85 mol-% to 200 mol-%), greater than 90 mol-% (e.g., from 90 mol-% to 150 mol-%), or greater than 100 mol-% (e.g., from 100 mol-% to 125 mol-%), of the FDCA-forming furanics. According to particular embodiments in which an excess stoichiometric amount of the co-feed is added, this may be an amount representing greater than 125 mol-% (e.g., from 125 mol-% to 1000 mol-%), greater than 150 mol-% (e.g., from 150 mol-% to 500 mol-%), or greater than 200 mol-% (e.g., from 200 mol-% to 400 mol-% or from 300 mol-% to 400 mol-%) of the FDCA-forming furanics.

Expressed in terms of a mass rather than a molar relationship, in certain embodiments of an oxidation feed that comprises (i) a dehydration product of one or more carbohydrates (e.g., having a six-carbon sugar unit), and (ii) a second monomer-forming co-feed (e.g., para-xylene), the latter may represent at least 1 wt-% of the combined amount of (i) and (ii). For example, the co-feed may be present in an amount representing from 1 wt-% to 75 wt-%, from 2 wt-% to 45 wt-%, or from 5 wt-% to 35 wt-%, of the combined amount of (i) and (ii).

In the case of co-feeding (i) FDCA-forming furanics and (ii) para-xylene to an oxidation reactor containing an oxidation catalyst and reactant oxygen, to provide a mixed monomer composition comprising the first and second monomers (e.g., FDCA and TPA), these feeds (i) and (ii) may be provided as separate streams (e.g., input at separate locations) to the same oxidation reactor. For example, the separate streams may enable a more desirable temperature profile within the oxidation reactor, or otherwise provide improved control over this temperature profile, such as by positioning or manipulating the exothermic heat release. Alternatively, the feeds (i) and (ii) may be provided as a combined feed stream to an oxidation reactor, such as in the case of combining a stream of para-xylene with the effluent of a dehydration reactor comprising the FDCA-forming furanics. In still further embodiments, portions of the feeds (i) and (ii) may be combined upstream of the oxidation reactor and/or added as separate streams to the oxidation reactor, depending on objectives relating to process efficiency and process control. As described above, the co-feeding may be further combined, in an integrated or non-integrated manner, with a further step, prior to the co-feeding, of dehydrating one or more carbohydrates to obtain the FDCA-forming furanics. This dehydrating may be performed with the one or more carbohydrates (e.g., selected from hexose sugars) being in a solution comprising, as a solvent, a lower carboxylic acid (e.g., acetic acid) or a lower alcohol (e.g., methanol or ethanol).

As described above, particular embodiments of the invention are directed to processing options, as well as overall processing flexibility, arising from the use of a second monomer-forming co-feed. Specific options relate to processing steps downstream of dehydrating and oxidizing steps for making the comprising two monomers, or mixed monomer composition. The dehydrating and oxidizing steps are further described below, as well as additional, and optional, steps of removing or modifying problematic humin species, color stabilizing, esterifying (or derivatizing in some other fashion, more generally), separating, and polymer forming, which may be performed in various orders and according to various configurations described, with further reference to specific orders and configurations illustrated in the figures. Having knowledge of the present disclosure, one skilled in the art would readily contemplate other processes having these additional steps, optionally with further steps, which other processes are nonetheless within the scope of the present invention.

Dehydrating Carbohydrates for Making FDCA-Forming Furanics

Representative processes comprise, prior to an oxidizing step, a dehydrating step for making FDCA-forming furanics as described above, all or a portion of which are used in (e.g., as a component of an oxidation feed for, or as a stream for co-feeding to), this oxidizing step. The dehydrating step may be performed batchwise, whereby the FDCA-forming furanics are recovered and intermittently transferred to the oxidizing step, but preferably the dehydrating step is performed continuously with continuous transfer. In any event, an upstream step of the process may therefore comprise dehydrating a dehydration feed comprising one or more carbohydrates having a six-carbon sugar unit, as described above. This dehydration feed (e.g., an aqueous fructose solution) may have a dry solids concentration from 5 wt-% to 50 wt-%, such as from 10 wt-% to 30 wt-% and/or may be prepared from a purified source of the six-carbon sugar such as fructose having a purity of at least 90 wt-% (e.g., 97 wt-% fructose). The dehydrating may occur in the presence of a bromine source and a solvent for the FDCA-forming furanics, and may be performed at an elevated temperature and for a time sufficient to generate the oxidation feed comprising FDCA-forming furanics, such as HMF and/or its derivatives. Depending on the solvent, the derivative(s) may include an ester derivative, an ether derivative, and/or HMF dimer. The oxidation feed, comprising some or all of the product formed in the dehydrating step (dehydration product) as a component, will generally also comprise at least a portion of the solvent. That is, all or a portion of the solvent, such as a mixture of acetic acid and water, that is used in the dehydrating step, may be passed to the oxidizing step, in addition to all or a portion of any water generated in this step. The solvent may otherwise comprise an alcohol such as methanol, ethanol, or a higher alcohol, or possibly a cyclic or heterocyclic hydrocarbon compound (e.g., dioxane). Solvent is preferably separated following the oxidizing step to provide, in addition to a mixed monomer composition or co-product as described herein, a solvent recycle stream back to the dehydrating step. The solvent recycle stream may contain FDCA-forming furanics, such that the total amount of FDCA-forming furanics in the dehydration product may include a portion that has been newly generated in a pass through the dehydrating step (i.e., based on a "per-pass conversion") and a portion that has been recycled back from the downstream oxidizing step.

In certain advantageous embodiments, the solvent used in the dehydrating step may be, or may comprise, all or a portion of the co-feed such as para-xylene. According to such embodiments, all or a portion of the co-feed added to the downstream oxidizing step may be present in the dehydration product, together with the FDCA-forming furanics. In the case of a portion of the co-feed being present, a second portion may be added directly to the oxidizing step (e.g., oxidation reactor), whereas a fresh, makeup portion of the co-feed may be added directly to the dehydrating step (e.g., dehydration reactor) or otherwise to a solvent recycle that is separated from an effluent of the oxidizing step (e.g., oxidation reactor) and fed back to the dehydrating step (e.g., dehydration reactor). Accordingly, the portion of the co-feed present in the dehydration product may represent a combined amount of the fresh, makeup portion and an amount present in the solvent recycle (e.g., at steady-state operation). In the case of adding at least a portion of the co-feed to the dehydrating step for use as a solvent, the overall material requirement and expenses associated with the use of a conventional solvent or component thereof (e.g., acetic acid) that does not undergo oxidation to form a second monomer, or oxidation at all, is advantageously reduced or even eliminated altogether. To the extent that co-feed added to the dehydrating step serves as an effective solvent for the FDCA-forming furanics and also becomes oxidized to a second monomer of a mixed monomer composition obtained in an effluent of the oxidizing step, those skilled in the art having knowledge of the present disclosure will appreciate that a number of operational advantages arise. For example, solvent recycle operating duties and associated expenses may be reduced or even eliminated altogether. In addition, productivity of the oxidizing step may be significantly increased, for example based on the molar production rate of one or more monomers (e.g., one of both of FDCA and TPA) per unit volume of the oxidation reactor.

The bromine source used in the dehydrating step can be any compound that provides bromide ions or radicals in the reaction mixture. Representative bromine sources include hydrogen bromide, hydrobromic acid, sodium bromide, potassium bromide, molecular bromine, benzyl bromide, and tetrabromoethane. In the case of hydrogen bromide being used, this compound, in the presence of the dehydration feed and solvent, may act as an acid catalyst in the dehydrating step, upon dissociation to form hydrobromic acid. In certain other embodiments, bromine sources such as 1-alkylpyridinium bromides and 1,3-dialkylimidazolium bromides may be useful as promoters in the presence of a solvent comprising acetic acid and water.

The step of dehydrating therefore provides a dehydration product, some or all of which may be used a component of the subsequent oxidizing step, together the stabilizing co-feed as described herein, used to form a second monomer. Particular methods for dehydrating are described, for example, in U.S. Pat. No. 10,538,499, wherein both of hydrobromic acid and acetic acid are present for the dehydration of especially fructose and then supplied for use in a subsequent Mid-Century oxidation step.

Removing Humins from the Dehydration Product

As described above, the step of dehydrating may result in the formation, in the dehydration product comprising FDCA-forming furanics, of humins as byproducts. Humins refer to highly colored, generally brown to black, amorphous or non-crystalline polymers resulting from the dehydration of sugars. The concentration of humins in the dehydration product will depend at least partly on conditions, and particularly reaction severity, used in the dehydrating step, such that this concentration may correlate with the per-pass conversion.

Insofar as humins are generally regarded as detrimental to the downstream oxidizing step as well as undesirable in terms of their ability to result in coloration of the bio-based polymer end product, representative processes may further comprise a step of separating at least a portion of the humins from the dehydration product, prior to the oxidizing step (e.g., to provide an oxidation feed having a reduced concentration of humins relative to the dehydration product). As described above, however, the reaction stabilizing effect of using para-xylene or other second monomer-forming co-feed with the dehydration product may lessen, or even eliminate, the need for humin removal, upstream of the oxidizing step. According to some embodiments, therefore, the dehydration product is not treated to remove humins, prior to the oxidizing step. For example, in specific embodiments, the humin content of FDCA-forming furanics obtained in the dehydrating step is not reduced by filtration or other suitable means of separating out at least some of the humins from the dehydration product, before co-feeding the dehydration product with para-xylene to an oxidation reactor. According to other embodiments, however, a purified portion of the dehydration product as described herein, which comprises purified HMF and/or other FDCA-forming furanics and which is obtained following the removal (e.g., by ultrafiltration) of a contaminant portion of the dehydration product that is enriched in humins, can nonetheless benefit from the addition of a co-feed (e.g., para-xylene) in terms of ameliorating reaction instability occurring under oxidation conditions and further in enabling retrofit scenarios to take advantage of underutilized para-xylene oxidation capacity.

According to particular embodiments, then, representative processes comprise removing at least a portion of humins in the dehydration product, prior to (upstream of) the oxidizing step (e.g., to provide the oxidation feed). If removal of humins is desired, the dehydration product may be subjected to filtration, such as using an ultrafiltration (UF) membrane, taking advantage of the general insolubility of humins in water. Other methods for removing humins from the dehydration product, or from other intermediate products in the overall synthesis of bio-based polymer, include distillation and sublimation. Particular methods for humin removal are described, for example, in U.S. Pat. No. 10,457,657.

Oxidizing the Oxidation Feed for Making a Co-Product, Including a Co-Monomer

Representative methods comprise contacting an oxidation feed, in the presence of oxygen, with an oxidation catalyst to provide a mixed monomer composition or co-product as described herein, which may comprise FDCA and a second monomer formed from the use of a co-feed such as para-xylene as a second component of the oxidation feed. As a first component of the oxidation feed, all or a portion of the dehydration product (e.g., comprising FDCA-forming furanics) may be used, such as a portion obtained following the removal of humins as described above. The oxidation feed may further comprise all or a portion of the solvent used to prepare the dehydration feed and/or at least one bromine-containing species. The oxygen may be obtained using, as a source, air, purified oxygen, or other oxygen-containing feed. The oxidizing step may be performed batchwise, but is preferably performed continuously, with at least the dehydration product (or a portion thereof), co-feed, and oxygen-containing feed, and optionally catalyst, being fed continuously to an oxidation reactor, and the mixed monomer composition being continuously withdrawn from this reactor.

Particular methods may comprise contacting the oxidation feed, as described above, with a metal-containing catalyst and the oxygen-containing feed at an elevated temperature for a time sufficient to produce, as an oxidation product, a mixed monomer composition comprising FDCA and/or its derivatives, a second monomer formed from oxidation of the co-feed (e.g., TPA formed from oxidation of para-xylene), solvent, and residual catalyst. The at least one bromine-containing species in the oxidation feed may provide some or substantially all of the bromine required for the oxidation step. Representative bromine-containing species include inorganic bromides such as HBr; metal bromides such as lithium bromide, sodium bromide, potassium bromide, magnesium bromide, calcium bromide, cobalt bromide, and manganese bromide; and organic bromides such as 5-(bromomethyl) furfural and derivatives thereof, and brominated furanic oligomers. A bromine source may be introduced to the oxidizing step (e.g., fed to the oxidation reactor), if necessary to supplement the bromine content that is provided by the bromine-containing species in the oxidation feed, which originate in the dehydrating step.

In the case of homogeneous (liquid phase) oxidation catalysts, metal-containing catalysts in particular can be effective for converting HMF and/or other FDCA-forming furanics (e.g., HMF esters and/or HMF ethers) in the oxidation feed (depending on the solvent used in the dehydrating step) to FDCA and/or its derivatives. Representative metal-containing catalysts may comprise one or more transition metals, such as either or both of Co and Mn, optionally in combination with Zr or Ce. The metal-containing catalyst may react with the bromine present in the bromine-containing species, as described above, to form metal bromides in situ. According to particular embodiments, the metal catalyst may be present in a reaction mixture that is contained in the oxidation reactor, such that the concentrations of the one or more transition metals are independently in the range from 5 wt-ppm to 10,000 wt-ppm, such as from 10 wt-ppm to 8,000 wt-ppm or from 50 wt-ppm to 5,000 wt-ppm. For example, Co may be present in the reaction mixture in a concentration from 10 wt-ppm to 10,000 wt-ppm, from 10 wt-ppm to 8,000 wt-ppm, from 59 wt-ppm to 5,900 wt-ppm, or from 2,000 to 4,000 wt-ppm. Mn may be present in the reaction mixture in a concentration from 5 wt-ppm to 10,000 wt-ppm, from 5 wt-ppm to 8,000 wt-ppm, from 55 wt-ppm to 5,500 wt-ppm, or from 200 to 1,000 wt-ppm. Bromine, from the bromine-containing species and/or bromine source, may be present in the reaction mixture from 0.1 wt-ppm to 20,000 wt-ppm, from 200 wt-ppm to 20,000 wt-ppm, from 10 wt-ppm to 10,000 wt-ppm, or from 1,000 wt-ppm to 2,000 wt-ppm.

Oxidizing conditions, or conditions maintained in the oxidizing reactor, may include a temperature from 120° C. to 250° C., such as from 170° C. to 190° C., and an oxygen partial pressure from 0.02 bar to 100 bar, from 0.02 bar to 21 bar, from 0.2 bar to 100 bar, or from 0.2 bar to 21 bar. The total absolute pressure in the oxidizing reactor may be from 1 bar to 200 bar, such as from 5 bar to 100 bar or from 10 bar to 20 bar. Molar yields of monomers from the oxidizing step, such as the molar yield of FDCA on the basis of the FDCA-forming furanics in the oxidation feed or the molar yield of TPA on the basis of para-xylene in the oxidation feed, may be at least 60%, at least 70%, at least 80%, at least 90%, or at least 95%. Following the oxidizing step, the resulting monomers such as FDCA and/or TPA may be separated from the oxidation reaction mixture, including the solvent, for further purification. At least a portion of the solvent, from which these monomers are separated, may then be recycled back to the dehydration reactor, together with at least a portion of unconverted FDCA-forming furanics. According to particular embodiments, since both FDCA and TPA are largely insoluble in acetic acid or in mixtures of acetic acid and water under mild conditions, separation of FDCA and/or TPA in such embodiments may be easily accomplished by filtration and/or centrifugation following their precipitation from the oxidation reaction mixture. Particular methods for oxidizing are described, for example, in U.S. Pat. No. 10,538,499.

Color Stabilizing a Mixed Monomer Composition or Separated Fraction, Optionally Before or after Derivatization (e.g., Esterification)

In general, the oxidizing step that is used to form a mixed monomer composition comprising two monomers may also generate color-forming byproducts to some extent, which contribute to an initial presence of color (preventing a desired, colorless appearance) and/or to forming color bodies over time, such as through aldol condensation reactions under acidic conditions that lead to increasing molecular weight. Particular color-forming byproducts are aldehyde derivatives of these monomers. For example, in the case of a mixed monomer composition or co-product comprising FDCA and TPA, this composition may further comprise, in independent amounts, generally from 0.1 wt-% to 15 wt-%, typically from 0.3 wt-% to 10 wt-%, and often from 1 wt-% to 3 wt-%, of (i) 5-formyl-2-furancarboxylic acid (FFCA) resulting from incomplete oxidation of FDCA and/or (ii) 4-carboxybenzaldehyde (4-CBA) resulting from incomplete oxidation of TPA. These byproducts, which are aldehyde derivatives of FDCA and TPA, respectively, are deleterious in terms of their color-forming tendency in both intermediate and end products. Likewise, in the case of separated fractions that are enriched in particular monomers such as either FDCA (in the case of an FDCA-enriched fraction) or TPA (in the case of a TPA-enriched fraction), such fractions may comprise aldehyde derivatives of monomers in which they are enriched, such as FFCA and/or 4-CBA, in independent amounts within the ranges given above.

In addition, according to some embodiments, the mixed monomer composition from the oxidation step and/or separated fractions of the mixed monomer composition that are enriched in either a first monomer or a second monomer, may be subjected to a further derivatization step calculated to prevent their participation in aldol condensation reactions leading to the development of unwanted color, for example, an esterification step. Nevertheless, in the case of an esterified mixed monomer composition (or esterified co-product) comprising 2,5-furandicarboxylic acid, dimethyl ester (FDME) as the principal ester derivative of FDCA, and dimethyl terephthalate (DMT) as the principal ester derivative of TPA, this composition may further comprise, in independent amounts, generally from 0.1 wt-% to 15 wt-%, typically from 0.3 wt-% to 10 wt-%, and often from 1 wt-% to 3 wt-%, of (i) 5-formyl-2-furancarboxylic acid methyl ester (FFME) resulting from the esterification of FFCA and (ii) 4-carboxybenzaldehyde methyl ester (4-CME) resulting from the esterification of 4-CBA. These byproducts, which are namely aldehyde-ester derivatives of FDCA and TPA, respectively, are, like their non-esterified counterparts, unfortunately also deleterious in terms of their color-forming tendency in both intermediate and end products. Likewise in the case of separated fractions that are enriched in particular ester derivative monomers, such as either FDME (in the case of an FDME-enriched fraction) or DMT (in the case of a DMT-enriched fraction), such fractions may also nevertheless comprise aldehyde-ester derivatives of the monomers in which they are enriched, such as FFME and 4-CME, in independent amounts within the ranges given above.

In view of the above description, representative processes include forming products resulting from steps from the dehydrating step to the polymer forming step, and these products may include one or more of: a mixed monomer composition; an esterified mixed monomer composition; a separated fraction that is enriched in a given monomer; or an esterified, separated fraction that is enriched in an ester derivative of such monomer. Any of such products may be subjected to a further color stabilizing step, in contemplation, for example, of the presence in even an esterified mixed monomer composition or in the esterified, separated monomer-enriched fractions of FFME and 4-CME or the presence in the underivatized mixed monomer composition or separated monomer-enriched fractions of aldehydes such as FFCA and 4-CBA, according to which the product is contacted with a color stabilizing medium, for example to reduce the content of one or more color-forming aldehydes and/or otherwise reduce the color of such product or render it less susceptible to color formation.

According to one embodiment, a color stabilizing step comprises contacting (i) a mixed monomer composition comprising two monomers, or (ii) a separated fraction thereof that may be enriched in a given monomer (relative to the mixed monomer composition from the oxidation step), (iii) an esterified mixed monomer composition comprising two ester derivatives of two monomers, or (iv) a separated fraction thereof that may be enriched in a given ester derivative of a monomer (relative to the esterified mixed monomer composition), with hydrogen, as the color stabilizing medium, to selectively hydrogenate a color-forming aldehyde byproduct, including any of the particular aldehyde byproducts described above. Color-forming aldehyde byproducts may be selectively hydrogenated under suitable hydrogenation conditions, whereby their aldehyde groups are converted to hydroxyalkyl groups to produce the corresponding hydroxyalkyl derivatives of these byproducts. In the case of a byproduct that is an aldehyde derivative of FDCA or of an ester derivative of FDCA, in which the aldehyde group is a formyl group, such byproduct may be selectively hydrogenated to its hydroxymethyl derivative. For example, in the case of FFCA (an aldehyde derivative of FDCA), this byproduct may be selectively hydrogenated to its hydroxymethyl derivative, 5-hydroxymethyl-2-furancarboxylic acid (HMFCA). In the case of FFME (an aldehyde derivative of FDME, which is an ester derivative of FDCA), this byproduct may be selectively hydrogenated to its hydroxymethyl derivative, 5-hydroxymethyl-2-furancarboxylic acid methyl ester (HMFME). In the case of 4-CBA (an aldehyde derivative of TPA), this byproduct may be selectively hydrogenated to its hydroxymethyl derivative, 4-hydroxymethyl-benzoic acid (4-HMBA). In the case of 4-CME (an aldehyde derivative of DMT, which is an ester derivative of TPA), this byproduct may be selectively hydrogenated to its hydroxymethyl derivative, methyl (4-hydroxymethyl)benzoate (4-HMMB).

In color stabilizing steps comprising contacting a given mixed monomer composition, separated fraction, or otherwise an esterified mixed monomer composition or separated fraction as described herein, with hydrogen, the contacting may be carried out in the presence of a hydrogenation catalyst, typically in solid form and comprising at least one noble metal, to produce a corresponding, stabilized composition (stabilized mixed monomer composition) or separated fraction, or otherwise a stabilized, esterified composition (stabilized, esterified mixed monomer composition) or separated fraction. Particular hydrogenation catalysts that can selectively hydrogenate aldehyde byproducts described herein, advantageously without substantially hydrogenating the furan rings or benzene rings of the corresponding monomers or ester derivative monomers, comprise the noble metals Pt and Ru, together with the promoter metal Sn. Other possible methods for the reduction of aldehyde byproducts are described in International Application PCT/US2018/041694 (published as WO 2019/014382), According to one embodiment, a color stabilizing step comprises contacting (i) a mixed monomer composition comprising two monomers, or (ii) a separated fraction thereof that may be enriched in a given monomer (relative to the mixed monomer composition), (iii) an esterified mixed monomer composition comprising two ester derivatives of two monomers, or (iv) a separated fraction thereof that may be enriched in a given ester derivative of a monomer (relative to the esterified mixed monomer composition), with a color stabilizing additive compound, as the color stabilizing medium. Color stabilizing additive compounds can advantageously reduce the extent of color formation during periods (e.g., prolonged storage periods) between the synthesis of monomer(s) and its/their use in the production of bio-based polymer(s) as described herein. The "contacting" with a color stabilizing additive compound may therefore result in a mixed monomer composition, separated fraction, or otherwise an esterified mixed monomer composition or separated fraction as described herein, comprising one or more color stabilizing additive compounds. Representative compositions may comprise, consist of, or consist essentially of, monomer(s) (e.g., FDCA and TPA in combination, or in separated fractions enriched in one or the other) or their ester derivative(s) (e.g., FDME and DMT in combination, or in separated fractions enriched in one or the other) and one or more color stabilizing additive compounds.

Since FDCA and TPA, as well as FDME, DMT, and other ester derivatives, are solid at room temperature, a color stabilizing step may comprise, for example, melting the monomer(s) or ester derivative(s) of interest, dispersing the desired color stabilizing additive compound(s) uniformly into the melt, and optionally solidifying the resulting, stabilized composition (e.g., by active cooling or simply allowing the composition to return to ambient conditions). Conveniently, however, the desired color stabilizing additive compound(s) may be introduced directly into (a) the oxidation feed for synthesis of the mixed monomer composition (b) any stream of a given mixed monomer composition, separated fraction, or otherwise an esterified mixed monomer composition or separated fraction as described herein, which is used in a polymer forming step, and/or (c) introduced into a reaction mixture of the polymer forming step, at any sub-step such as (i) esterifying or transesterifying, and (ii) polymerizing by polycondensation.

Representative color stabilizing additive compounds include substituted phenols, which refer to compounds having at least one phenol moiety, but possibly two or more phenol moieties, in which the benzene ring(s) of such moiety or moieties have at least one substituent, other than the hydroxyl substituent. Particular examples of such substituents are alkoxy and alkyl substituents, with methoxy and tert-butyl substituents being preferred. Therefore, examples of substituted phenols include alkoxy-substituted (e.g., methoxy-substituted) and alkyl-substituted (e.g., tert-butyl-substituted) phenols, which are namely compounds having at least one phenol moiety, but possibly two or more phenol moieties, with one or more alkoxy (e.g., methoxy) and alkyl (e.g., tert-butyl) substituents, respectively. In the case of tert-butyl-substituted phenols, these compounds are often referred to as "hindered phenols," in view of the steric hindrance resulting from the geometry of these substituents.

Substituted phenols include butylated hydroxyanisole (BHA); 2,6-dimethoxyphenol (DMP); 2,6-di-tert-butyl-4-methoxylphenol (DTMP); pentaerythritol tetrakis[3-[3,5-di-tert-butyl-4-hydroxyphenyl]propionate (PETC); 2-tert-butylhydroquinone (TBHQ); ethylenebis (oxyethylene) bis-(3-(5-tert-butyl-4-hydroxy-m-tolyl)-propionate); and octadecyl-3-(3,5-di-tert-butyl-4-hydroxyphenyl)-propionate. Of these compounds, (i) BHA, DMP, and DTMP are methoxy-substituted phenols, and (ii) DTMP, PETC, TBHQ, ethylenebis (oxyethylene) bis-(3-(5-tert-butyl-4-hydroxy-m-tolyl)-propionate); and octadecyl-3-(3,5-di-tert-butyl-4-hydroxyphenyl)-propionate are tert-butyl-substituted phenols. Other color stabilizing additive compounds include phenyl-substituted amines (e.g., 4,4'-bis($\alpha,\alpha$-dimethylbenzyl) diphenylamine (XDPA)), phosphites (e.g., tris(2,4-di-tert-butylphenyl)phosphite), and antioxidant vitamins (e.g., ascorbic acid). The compound PETC is commercially available as Irganox®1010 (BASF) or Dovernox®10 (Dover Chemical Corp.); the compound ethylenebis (oxyethylene) bis-(3-(5-tert-butyl-4-hydroxy-m-tolyl)-propionate) is commercially available as Irganox®245 (BASF); the compound tris(2,4-di-tert-butylphenyl)phosphite is commercially available as Irgafos®168 (BASF); and the compound octadecyl-3-(3,5-di-tert-butyl-4-hydroxyphenyl)-propionate is commercially available as Irganox®1076 (BASF) or Dovernox®76 (Dover Chemical Corp.).

A color stabilizing step may include the use of a combination of color stabilizing additive compounds, as a color stabilizing medium, including a combination of any of the compounds and/or classes of compounds as described above, such as a combination of one or more tert-butyl-substituted phenols and one or more phosphites. For example, the combination of 50 wt-% PETC and 50 wt-% tris(2,4-di-tert-butylphenyl)phosphite is commercially available as Irganox®B255 (BASF). The combination of 20 wt-% octadecyl-3-(3,5-di-tert-butyl-4-hydroxyphenyl)-propionate and 80 wt-% tris(2,4-di-tert-butylphenyl)phosphite is commercially available as Irganox®B900 (BASF). The combination of 50 wt-% PETC and 50 wt-% tris(2,4-di-tert-butylphenyl)phosphite is commercially available as Irganox®B225 (BASF).

One or more color stabilizing additive compounds may be present in products such as (i) a mixed monomer composition comprising two monomers, or (ii) a separated fraction thereof that may be enriched in a given monomer (relative to the mixed monomer composition), (iii) an esterified mixed monomer composition comprising two ester derivatives of two monomers, (iv) a separated fraction thereof that may be enriched in a given ester derivative of a monomer (relative to the esterified mixed monomer composition), or (v) a bio-based polymer as described herein. Such bio-based polymer may have both furandicarboxylate moieties and terephthalate moieties, or otherwise may have all or substantially all furandicarboxylate moieties, or all or substantially all terephthalate moieties. In any such product, the amount, or combined amount in the case of a combination, may be generally from 10 wt-ppm to 1 wt-%, typically from 50 wt-ppm to 2000 wt-ppm, and often from 50 wt-ppm to 1500 wt-ppm. According to preferred embodiments, the additive BHA may be present in any such product (e.g., comprising both FDCA and TPA to stabilize these monomers) in an amount from 100 wt-ppm to 500 wt-ppm, or the additive Irganox®245 may be present in any such product (e.g., comprising both FDCA and TPA to stabilize these monomers) in an amount from 800 wt-ppm to 1200 wt-ppm. These and other color stabilizing additive compounds, and other aspects relating to their use in the color stabilization of process streams for forming bio-based polymers, are described in WO 2019/246034).

In processes described herein, steps of color stabilizing and esterifying are optional and may be performed in either order, depending on a given processing objective. Accordingly, for purposes of the present disclosure and with reference to the drawing figures, it should be understood that any "stabilized, esterified" composition (stabilized, esterified mixed monomer composition) comprising two ester derivative monomers (e.g., both FDME and DMT), or any "stabilized, esterified" fraction enriched in a given ester derivative monomer (e.g., FDME or DMT), as described herein, can be equivalently, (i) in the case of omitting the color stabilizing step, an "esterified" mixed monomer composition comprising two ester derivative monomers (e.g., both FDME and DMT), or an "esterified" fraction enriched in a given ester derivative monomer (e.g., FDME or DMT), or (ii) in the case of omitting the esterifying step, a "stabilized" mixed monomer composition comprising two monomers (e.g., both FDCA and TPA), or a "stabilized" fraction enriched in a given monomer (e.g., FDCA or TPA). For purposes of the present disclosure and with reference to the drawing figures, it should also be understood that forming a "stabilized, esterified" composition (stabilized, esterified mixed monomer composition) comprising two ester derivative monomers (e.g., both FDME and DMT), or a "stabilized, esterified" fraction enriched in a given ester derivative monomer (e.g., FDME or DMT) can be achieved by first color stabilizing and then esterifying, by first esterifying and then color stabilizing, or by performing both steps simultaneously (e.g., by contacting an esterification reaction mixture with a color stabilizing medium as described herein).

Steps of esterifying monomers such as FDCA and TPA, for forming ester derivatives, comprise reacting these monomers with an esterifying agent such as an alcohol, for example methanol if a dimethyl ester is desired or ethanol if a diethyl ester is desired, or possibly phenol, if a diphenyl ester is desired. The reaction of FDCA and/or TPA, or other monomer(s), with the appropriate alcohol, or phenol, may be carried out in an esterification reaction mixture including a high boiling point solvent (e.g., dimethyl sulfoxide, dimethylacetamide, sulfolane, FDME, γ-butyrolactone, isosorbide or its dimethyl ether, propylene carbonate, adipic acid, isophorone, ethyl phenyl ether, diphenyl ether, dibenzyl ether, aromatic 200 fluid, butyl phenyl ether, methyl heptyl ketone, ethyl phenyl ketone, 2'-hydroxyacetophenone, decahydronaphthalene, tetrahydronaphthalene, etc.) under suitable esterification conditions. These may include a temperature from 30° C. (86° F.) to 350° C. (662° F.) and a pressure from atmospheric pressure to 3.5 megapascal (MPa), and the esterification reaction may be performed together with distillation (according to a reactive distillation process) for separation of the FDME, DMT, or other ester derivative.

In preferred embodiments, a step of esterifying (i) a mixed monomer composition (or stabilized mixed monomer composition) comprising two monomers, or (ii) a separated fraction thereof (or stabilized, separated fraction thereof) that may be enriched in a given monomer (relative to the mixed monomer composition), comprises reacting any such mixed monomer composition or separated fraction thereof with methanol as the esterifying agent. For example, in the case of a mixed monomer composition (or stabilized mixed monomer composition) resulting from an oxidizing step and comprising both FDCA and TPA, esterifying such mixed monomer composition (or stabilized mixed monomer composition) may comprise reacting it with methanol to provide an esterified mixed monomer composition (or stabilized esterified mixed monomer composition) comprising FDME and DMT. According to particular embodiments, esterification of a mixed monomer composition or stabilized composition is desirable as the ester derivative monomers, e.g., FDME and DMT have lower boiling points relative to their parent dicarboxylic acid compounds, and are more amenable to separation by distillation in view of this and their relative volatilities. In the case of any step(s) of esterifying as described herein generally and/or with respect to the embodiments illustrated in the figures, it is possible that further, downstream step(s) may be used to convert the ester derivative(s) (e.g., FDME and/or DMT) obtained from the esterifying step back to the parent, carboxylic acid(s) (e.g., FDCA and/or TPA), for example prior to polymer forming step(s) as described herein.

In view of the processing options described herein with respect to steps of color stabilizing, esterifying, and/or separating, it can be appreciated that representative mixed monomer compositions, following oxidation, may comprise, as color-forming byproducts, an aldehyde derivative of FDCA (e.g., FFCA) and an aldehyde derivative of TPA (e.g., 4-CBA), and processes may comprise selectively hydrogenating one or both of the aldehyde derivative of FDCA and the aldehyde derivative of TPA (e.g., reduce their concentrations in a given process stream to improve color and/or color stability of a copolymer ultimately produced from that process stream). This step of selectively hydrogenating one or both of the aldehyde derivative of FDCA and the aldehyde derivative of TPA may occur following a separation of the mixed monomer composition into an FDCA-enriched fraction and a TPA-enriched fraction. According to other embodiments in which the mixed monomer composition comprises an aldehyde derivative of FDCA and an aldehyde derivative of TPA, processes may further comprise, in a step of esterifying one or both of the FDCA and TPA, producing, as further color-forming byproducts, one or both of an aldehyde derivative of an ester derivative of FDCA (e.g., FFME) and an aldehyde derivative of an ester derivative of TPA (e.g., 4-CME). Representative processes in this case may further comprise selectively hydrogenating one or both of the aldehyde derivative of the ester derivative of FDCA and the aldehyde derivative of the ester derivative of TPA (e.g., reduce their concentrations in a given process stream to improve color and/or color stability of a copolymer ultimately produced from that process stream). In the case of esterifying both of the FDCA and TPA, this may comprise esterifying these materials concurrently in the mixed monomer composition by reaction with an esterifying agent in the presence or absence of a suitable esterification catalyst, to provide an esterified mixed monomer composition comprising both the aldehyde derivative of the ester derivative of FDCA and the aldehyde derivative of the ester derivative of TPA. Esterifying both of the FDCA and TPA (e.g., by combining the mixed monomer composition with an esterifying agent (alcohol) in the presence or absence of an esterification catalyst and under corresponding process conditions for carrying out an esterification of FDCA and TPA in the mixed monomer composition) may occur upstream of a separation of the esterified mixed monomer composition into a first fraction enriched in an ester derivative of FDCA and a second fraction enriched in an ester derivative of TPA. Alternatively, in the case of esterifying one or both of the FDCA and TPA, this may comprise esterifying one or both of an FDCA-enriched fraction and a TPA-enriched fraction, by reaction with an esterifying agent, downstream of a separation of the mixed monomer composition into the FDCA-enriched fraction and the TPA-enriched fraction.

Polymer Forming from a Mixed Monomer Composition/ Oxidation Product or from Separated Monomer-Enriched Fractions Any of the mixed monomer oxidation products (e.g., comprising both FDCA and TPA) or separated fractions thereof (e.g., enriched in FDCA or enriched in TPA, relative to the mixed monomer oxidation products from which the fractions derive) or esterified mixed monomer compositions (e.g., comprising both FDME and DMT) or separated fractions thereof (e.g., enriched in FDME or enriched in DMT, relative to the esterified mixed monomer oxidation products from which the fractions derive), optionally having been subjected to a color stabilizing step, may be used for forming polymers. Forming a polymer from a combined monomer oxidation product directly can yield a copolymer having both FDCA-related moieties (e.g., furandicarboxylate moieties) and TPA-related moieties (e.g., terephthalate moieties), whereas forming a polymer from a separated fraction thereof can yield a copolymer having FDCA-related moieties and being substantially free of (or at least having less of) TPA-related moieties (e.g., providing a substantially bio-based copolymer wherein the p-xylene is conventionally petroleum-based), or otherwise a copolymer having TPA-related moieties and being substantially free of (or at least having less of) FDCA-related moieties (which might be desirable for some practitioners given the well-established infrastructure for recycling PET and in consideration of the difficulty of converting users to a new polymer). In general, representative polymer forming steps can include, for the production of polyesters, (A)(i) esterifying a mixed monomer composition or separated fraction thereof, as described herein, or (A)(ii) transesterifying an esterified mixed monomer composition or separated fraction thereof, as described herein, and (B) polymerizing by polycondensation.

Representative polyester polymer forming steps involve the polymerization of monomers and ester derivative monomers described herein, and particularly the monomers FDCA and/or TPA and the ester derivative monomers FDME and/or DMT, with suitable co-monomers such as diols. For example, ethylene glycol may be used as the co-monomer to produce PEF (from FDCA or FDME) or PET (from TPA or DMT). The co-monomer 1,3-propanediol may be used to produce poly(trimethylene furan dicarboxylate) (PTF) (from FDCA or FDME) or polypropylene terephthalate (from TPA or DMT).

Particular methods may comprise producing a precursor composition comprising a prepolymer that is an esterified intermediate such as the reaction product of FDCA and/or TPA with the co-monomer, or a transesterified intermediate such as the reaction product of FDME and/or DMT with the co-monomer. The prepolymer, whether an esterified intermediate or transesterified intermediate, is functionalized with terminal alcohol groups (e.g., rather than terminal carboxylate groups of TPA, or terminal methyl groups of FDME or DMT) and therefore may then be subjected to polycondensation to provide a copolymer as described herein, and particularly a poly(alkylene furan dicarboxylate) polymer, a poly(alkylene terephthalate) polymer, or a copolymer comprising both alkylene furan dicarboxylate residues and alkylene terephthalate (or alkylene terephthalate) residues. Likewise, aldehyde derivatives described herein, present in monomer compositions (e.g., FFCA in an FDCA monomer composition, 4-CBA in a TPA monomer composition, FFME in an FDME monomer composition, or 4-CME in a DMT monomer composition) that are used to produce precursor compositions, will become esterified or transesterified, under conditions used to produce the precursor composition. Nonetheless, insofar as the aldehyde group is retained in such byproducts in the precursor composition, by subjecting this composition to a color stabilizing step as described herein, i.e., by contacting with hydrogen or a color stabilizing additive compound, either of which can serve as a color stabilizing medium, the color stabilizing benefits as described herein may be attained.

Processes for producing a polyester polymer (e.g., copolyester) can therefore include both a first, esterification or transesterification step to produce an intermediate (prepolymer), followed by a second, polycondensation step. The first step may be catalyzed by an esterification/transesterification catalyst at a temperature from 150° C. (302° F.) to 250° C. (482° F.), and carried out until the concentration of the starting monomer(s) or ester derivative monomer(s) is reduced to less than 3 mol-%. The catalyst may comprise an organotin(IV) compound, present in a concentration from 0.01 mol-% to 0.2 mol-% in a polymer forming reaction mixture, relative to the starting monomer(s) or ester derivative(s). The prepolymer, as described herein, may therefore be the reaction product of two diol monomers and one monomer bearing either a furandicarboxylate moiety or a terephthalate (benzenecarboxylate) moiety that is ultimately present in the backbone of the resulting polymer.

Other diols of interest for forming the intermediate (prepolymer) include those, like FDCA, which may be bio-derived, such as in the case of isohexides. These compounds are bicyclic, rigid diols that differ only in the orientation of the hydroxyl groups at $C_2$ and $C_5$ ring positions, and they can be obtained by cyclodehydration of hexitols. For example, isomannide can be obtained (endo-endo) from mannitol, isosorbide (exo-endo) can be obtained from sorbitol, and isoidide (exo-exo) can be obtained from iditol. Regardless of the particular diol, the intermediate (prepolymer) that is formed may optionally be isolated from the reaction mixture of the first reaction step, although generally this is not necessary. The second step of polycondensation may be catalyzed and performed under reduced pressure (e.g., 100 Pascals (Pa) or less), at a temperature in the range of the melting point of the resulting copolymer to 30° C. (54° F.) above this temperature, and preferably at a temperature of at least 180° C. (356° F.). The polycondensation catalyst may comprise a tin(II) compound, such as tin(II) oxide or an organotin(II) compound. Otherwise, a catalyst based on titanium may be employed, such as titanium or a chelated titanium compound, having various ligands that can include alkoxides, for example propoxide or tert-butoxide. Representative catalysts are therefore titanium (IV) propoxide and titanium (IV) tert-butoxide.

As described above, FDCA and/or TPA, whether present together or present in separated fractions enriched in given monomer, may be used in forming polymers other than polyester polymers. For example, polyamide polymers may be formed in the case of reacting one or both of FDCA and TPA, separately or in combination, with a co-monomer having at least two amino groups (e.g., a diamine), to produce a polyamide having one or both of FDCA-related moieties and TPA-related moieties. Suitable co-monomers include aliphatic diamines such as hexamethylene diamine and aromatic diamines such as paraphenylene diamine. As also described above, a derivative of FDCA and/or a derivative of TPA, whether present together or present in separated fractions enriched in given monomer, may be used in forming polyester polymers. For example, polyester polymers may be formed in the case of reacting, as a co-monomer, a hydroxyl (alcohol) derivative of one or both of FDCA and TPA (e.g., a diol derivative of one or both of FDCA and TPA), separately or in combination, with a polyacid (e.g., FDCA or TPA) or its ester derivative thereof to produce a polyester having one or both of FDCA-related moieties and TPA-related moieties. Suitable co-monomers that are hydroxyl derivatives of FDCA include furan 2,5-diol and furan 2,5-dimethanol, and suitable co-monomers that are hydroxyl derivatives of TPA include hydroquinone and benzene 1,4-dimethanol.

As further described above, a derivative of FDCA and/or a derivative of TPA, whether present together or present in separated fractions enriched in given monomer, may be used in forming polymers other than polyester polymers. For example, polyurethane polymers may be formed in the case of reacting, as a co-monomer, a hydroxyl (alcohol) derivative of one or both of FDCA and TPA (e.g., a diol derivative of one or both of FDCA and TPA), separately or in combination, with a polyisocyanate to produce a polyurethane having one or both of FDCA-related moieties and TPA-related moieties. Suitable co-monomers that are hydroxyl derivatives of FDCA include those described above with respect to the formation of polyester polymers. Suitable polyisocyanates include diisocyanates, and in particular aromatic diisocyanates such as toluene diisocyanate, methylene diphenyl diisocyanate, and polymeric methylene diisocyanates. In other embodiments, polyamide polymers may be formed in the case of reacting, as a co-monomer, an amino derivative of one or both of FDCA and TPA (e.g., a diamino derivative of one or both of FDCA and TPA), separately or in combination, with a polyacid (e.g., FDCA or TPA) to produce a polyamide having one or both of FDCA-related moieties and TPA-related moieties. Suitable co-monomers that are amino derivatives of FDCA include furan 2,5-diamine and furan 2,5-dialkyl amines such as furan 2,5-dimethanamine, and suitable co-monomers that are amino derivatives of TPA include benzene 1,4-diamine and benzene 1,4 dialkylamines such as benzene 1,4-dimethanamine. In other embodiments, polyamide polymers may be formed in the case of reacting an acyl derivative of one or both of FDCA and TPA (e.g., a diacyl chloride derivative of one or both of FDCA and TPA), separately or in combination, with a co-monomer having at least two amino groups (e.g., a diamine), to produce a polyamide having one or both of FDCA-related moieties and TPA-related moieties. Suitable acyl derivatives of FDCA include furan 2,5-diformyl chloride and furan 2,5-dialkyl chlorides such as furan 2,5-diacetyl chloride, and suitable acyl derivatives of TPA include benzene 1,4-diformyl chloride and benzene 1,4 dialkyl chlorides such as benzene 1,4-diacetylchloride. Suitable co-monomers include aliphatic diamines such as hexamethylene diamine and aromatic diamines such as paraphenylene diamine. In other embodiments, polyurethane polymers may be formed in the case of reacting an isocyanate derivative of one or both of FDCA and TPA (e.g., a diisocyanate derivative of one or both of FDCA and TPA), separately or in combination, with a co-monomer having at least two hydroxyl groups (e.g., a diol), to produce a polyurethane having one or both of FDCA-related moieties and TPA-related moieties. Suitable isocyanate derivatives of FDCA include furan 2,5-diisocyanate and furan 2,5-dialkyl isocyanates such as furan 2,5-dimethanisocyanate, and suitable isocyanate derivatives of TPA include benzene 1,4-diisocyanate and benzene 1,4 dialkyl isocyanates such as benzene 1,4-dimethanisocyanate. Suitable co-monomers include diols such as those described above for forming an intermediate (prepolymer) used to ultimately produce a polyester polymer. In still other embodiments polycarbonate polymers may be formed in the case of reacting a hydroxyl (alcohol) derivative of one or both of FDCA and TPA (e.g., a diol derivative of one or both of FDCA and TPA), separately or in combination, with phosgene to produce a polycarbonate having one or both of FDCA-related moieties and TPA-related moieties. Suitable hydroxyl derivatives of FDCA include those described above with respect to co-monomers the formation of polyester polymers.

Exemplary Embodiments for Making a Mixed Monomer Composition Comprising FDCA and TPA The process illustrated in FIG. 1 comprises steps for making a mixed monomer composition comprising FDCA and TPA as described above, including steps of dehydrating 100, oxidizing 200, optional color stabilizing 50, optional esterifying 55, and polymer forming 300. According to this figure, dehydration feed 10 comprising one or more carbohydrates having a six-carbon sugar unit is subjected to dehydrating 100 to provide dehydration product 12, all or a portion of which may be used as a component of the oxidation feed. In some embodiments, a contaminant portion of dehydration product 12, such as a portion 11 that is concentrated in humins (e.g., in a filtration retentate) may be removed in order to provide purified portion 12' of dehydration product 12 that may be used as a component of, or possibly the entire, the oxidation feed. The depicted process may comprise contacting dehydration product 12 or purified portion 12' thereof in the presence of oxygen, such as introduced in oxygen-containing feed 16 (e.g., air), with an oxidation catalyst. According to one embodiment, a second component of the oxidation feed, in addition to dehydration product 12 or purified portion 12' thereof, is para-xylene-containing feed 14. Mixed monomer composition 18 comprising (i) FDCA from the oxidation of dehydration product 12 or purified portion 12' thereof, and (ii) TPA from the oxidation of para-xylene, is withdrawn from oxidizing step 200 (e.g., an oxidation reactor). All or a portion of the mixed monomer composition (or oxidation product) 18 may be used in polymer forming step 300, optionally following color stabilizing 50 to provide a stabilized composition 20 and/or esterifying 55, for example to provide a stabilized, esterified composition 22 (if both steps are used). As described herein, these optional steps may be performed in either order. Mixed monomer composition 18 may be obtained from oxidizing step 200, for example in an effluent of an oxidation reactor, from which a solvent recycle 15 is separated (e.g., based on a relative insolubility, of monomers in mixed monomer composition 18, in a solvent or solvent system for FDCA-forming furanics in dehydration product 12). All or a portion of solvent recycle 15 may be fed back or returned to dehydrating 100 step (e.g., a dehydration reactor), and a fresh, makeup portion 17 of solvent may be added to solvent recycle 15 or otherwise directly to dehydrating 100 step.

According to another embodiment, all or a portion of the para-xylene added to the downstream oxidizing 200 step may be present in dehydration product 12 or purified portion 12' thereof. In the case of a portion of the para-xylene being present, para-xylene-containing feed 14 may represent a second portion that is added directly to oxidizing 200 step (e.g., oxidation reactor), whereas fresh, makeup portion 17 of solvent may represent a fresh, makeup portion of para-xylene that is added to solvent recycle 15 or otherwise directly to dehydrating 100 step (e.g., dehydration reactor). Accordingly, the para-xylene present in dehydration product 12 may represent a combined amount of fresh, makeup portion 17 and an amount present in solvent recycle 15 (e.g., at steady-state operation). In the case of adding at least a portion of the para-xylene requirement of the process to the dehydrating step for use as a solvent, a number of advantages may be gained in terms of various operational efficiencies, as described above.

Representative processes may comprise (A) color stabilizing 50 the mixed monomer composition (or oxidation product) 18 by adding (or contacting with) color stabilizing medium 19, to provide a stabilized composition 20 comprising FDCA and TPA; and (B) optionally following (A), esterifying 55 the stabilized composition 20 by reaction with esterifying agent 21, to provide a stabilized, esterified composition 22 comprising ester derivatives of FDCA and TPA (e.g., the diesters FDME and DMT). Following (A), the process may for the purpose of making a copolyester from FDCA and TPA further comprise reacting stabilized composition 20 comprising FDCA and TPA with a co-monomer 24 having at least two hydroxyl groups (e.g., a diol) to produce a stabilized, co-esterified intermediate (prepolymer) composition comprising (i) a first esterified intermediate that is a reaction product of FDCA and the co-monomer and (ii) a second esterified intermediate that is a reaction product of TPA and the co-monomer, and polymerizing the stabilized, co-esterified intermediate composition by polycondensation of the first and second esterified intermediates to yield copolymer product 26 comprising a copolymer having furandicarboxylate moieties and terephthalate moieties. The steps of reacting with co-monomer 24, followed by polymerizing by polycondensation are sub-steps of polymer forming 300. Following (B), the process may further comprise reacting a stabilized, esterified composition 22 comprising the ester derivatives of FDCA and TPA with co-monomer 24 having at least two hydroxyl groups (e.g., a diol) to produce a stabilized, co-transesterified intermediate (prepolymer) composition comprising (i) a first transesterified intermediate that is a reaction product of the ester derivative of FDCA and co-monomer 24 and (ii) a second transesterified intermediate that is a reaction product of the ester derivative of TPA and co-monomer 24, and polymerizing the stabilized, co-transesterified intermediate composition by polycondensation of the first and second transesterified intermediates to yield copolymer product 26 comprising a copolymer having furandicarboxylate moieties and terephthalate moieties. The steps of reacting with co-monomer 24, followed by polymerizing by polycondensation are sub-steps of polymer forming 300.

In the case of esterifying and color stabilizing being performed in the opposite order, the process may comprise (A) esterifying the mixed monomer composition 18 by reaction with esterifying agent 21, to provide an esterified mixed monomer composition comprising ester derivatives of both FDCA and TPA, and (B) optionally following (A), color stabilizing the esterified mixed monomer composition (or mixed ester composition) by adding color stabilizing medium 19 to provide a stabilized composition 22 comprising stabilized ester derivatives of both FDCA and TPA. Following (A), the process may, for purposes of preparing a copolyester, further comprise reacting the esterified mixed monomer composition comprising ester derivatives of both FDCA and TPA with a co-monomer 24 having at least two hydroxyl groups (e.g., a diol) to produce a co-transesterified intermediate (prepolymer) composition comprising (i) a first transesterified intermediate that is a reaction product of an ester derivative of FDCA and the co-monomer and (ii) a second transesterified intermediate that is a reaction product of an ester derivative of TPA and the co-monomer, and polymerizing the co-transesterified intermediate composition by polycondensation of the first and second esterified intermediates to yield copolymer product 26 comprising a copolymer having furandicarboxylate moieties and terephthalate moieties. The steps of reacting with co-monomer 24, followed by polymerizing by polycondensation are sub-steps of polymer forming 300. Following (B), the process may further comprise reacting the stabilized, esterified composition 22 comprising ester derivatives of both FDCA and TPA with co-monomer 24 having at least two hydroxyl groups (e.g., a diol) to produce a stabilized, co-transesterified intermediate (prepolymer) composition comprising (i) a first transesterified intermediate that is a reaction product of an ester derivative of FDCA and the co-monomer and (ii) a second transesterified intermediate that is a reaction product of an ester derivative of TPA and the co-monomer, and polymerizing the stabilized, co-transesterified intermediate composition by polycondensation of the first and second transesterified intermediates to yield copolymer product 26 comprising a copolymer having furandicarboxylate moieties and terephthalate moieties. The steps of reacting with co-monomer 24, followed by polymerizing by polycondensation are sub-steps of polymer forming 300.

The process illustrated in FIG. 2 comprises steps as illustrated in FIG. 1 for making a mixed monomer composition or co-product comprising FDCA and TPA, including steps of dehydrating 100, oxidizing 200, optional color stabilizing 50, and optional esterifying 55. According to this figure, all or a portion of the mixed monomer composition 18, optionally stabilized composition 20, or optionally stabilized, esterified composition 22, is used in a step of separating 60, for example to provide fractions that may be enriched in one monomer or relative to another monomer, or ester derivatives of one monomer relative to the ester derivatives of the other monomer. As used herein, the characteristic of being "enriched in" refers to having a higher concentration of a given monomer or the ester derivatives of that monomer, relative to the product before undergoing separation. A fraction that is enriched in a given monomer or the ester derivatives of that monomer (e.g., FDCA, TPA, the mono- and diester derivatives of FDCA and the mono- and diester derivatives of TPA), may comprise at least 50 wt-%, at least 75 wt-%, or at least 90 wt-%, of that monomer or of the ester derivatives of that monomer. A fraction being enriched in a given monomer or the ester derivatives of a given monomer may therefore also be "depleted in" (have a lower concentration of) a given monomer or the ester derivatives of a given monomer that is also present in the product before undergoing separation. For example an FDCA-enriched fraction may be depleted in TPA, such that this fraction may be substantially free of TPA (e.g., may comprise less than 5 wt-%, less than 3 wt-%, or less than 1 wt-%) of this compound. A TPA-enriched fraction may be depleted in FDCA, such that this fraction may be substantially free of FDCA (e.g., may comprise less than 5 wt-%, less than 3 wt-%, or less than 1 wt-%) of this compound. A fraction enriched in the ester derivatives of FDCA (or an esterified FDCA-enriched fraction) may be depleted in the ester derivatives of TPA, such that the fraction may be substantially free of these mono- and diester derivatives (e.g., may comprise less than 5 wt-%, less than 3 wt-%, or less than 1 wt-%) of the ester derivatives of TPA. A fraction enriched in the ester derivatives of TPA (or an esterified TPA-enriched fraction) may be depleted in the ester derivatives of FDCA such that the fraction may be substantially free of these ester derivatives (e.g., may comprise less than 5 wt-%, less than 3 wt-%, or less than 1 wt-%) of the mono- and diester derivatives of FDCA.

The step of separating 60, according to the embodiment of FIG. 2 may be performed according to any of a number of techniques, such as fractional solidification (based on melting point difference); crystallization, optionally following extraction in aqueous or organic media (based on solubility difference); adsorbent or chromatographic methods, including simulated moving bed (SMB) chromatography (based on molecular size/structure difference); and distillation, optionally with a stripping gas or extracting solvent (based on relative volatility difference). According to one embodiment, a step of esterifying 55 renders the resulting ester derivative monomers more amenable to separation by distillation. Accordingly, separating 60 may include the distillation of the esterified mixed monomer composition (or esterified oxidation product) 22 (optionally following a color stabilizing step 50) into a first fraction 251 enriched in the ester derivatives of FDCA (e.g., FDME) and a second fraction 252 enriched in the ester derivatives of TPA (e.g., DMT). In particular embodiments, the step of separating 60 may be used to separate mixed monomer composition 18 (optionally following color stabilizing 50) into a first, FDCA-enriched fraction 251 and a second, TPA-enriched fraction 252. Following the step of separating 60, optional steps of color stabilizing 501/502, optional steps of esterifying 551/552, and steps of polymer forming 301/302 may be performed on the separated fractions, in the manner described above.

According to possible embodiments illustrated in FIG. 2, therefore, processes may further comprise (A) color stabilizing a first, FDCA-enriched fraction 251 by adding color stabilizing medium 19 to provide a stabilized FDCA-enriched fraction 201, and (B) optionally following (A), esterifying the stabilized FDCA-enriched fraction 201 by reaction with esterifying agent 21, to provide a stabilized, esterified FDCA-enriched fraction 221 comprising an ester derivative of FDCA. Following (A), the process may further comprise reacting the stabilized FDCA-enriched fraction 201 with co-monomer 24 having at least two hydroxyl groups (e.g., a diol) to produce a stabilized, esterified intermediate (prepolymer) composition comprising (i) a first esterified intermediate that is a reaction product of FDCA and the co-monomer and being substantially free of (ii) a second esterified intermediate that is a reaction product of TPA and the co-monomer, and polymerizing the stabilized, esterified intermediate composition by polycondensation of the first esterified intermediate to yield a polymer product 261 comprising a polyester having furandicarboxylate moieties and being substantially free of terephthalate moieties. The steps of reacting with co-monomer 24, followed by polymerizing by polycondensation are sub-steps of polymer forming 301. Following (B), the process may further comprise reacting the stabilized, esterified FDCA-enriched fraction 221 comprising an ester derivative of FDCA (especially the diester) with co-monomer 24 having at least two hydroxyl groups (e.g., a diol) to produce a stabilized, transesterified intermediate (prepolymer) composition comprising (i) a first transesterified intermediate that is a reaction product of a mono- and/or diester derivative of FDCA and the co-monomer and being substantially free of (ii) a second transesterified intermediate that is a reaction product of an ester derivative of TPA and the co-monomer, and polymerizing the stabilized, transesterified intermediate composition by polycondensation of the first transesterified intermediate to yield polyester product 261 comprising a polyester having furandicarboxylate moieties and being substantially free of terephthalate moieties. The steps of reacting with co-monomer 24, followed by polymerizing by polycondensation are sub-steps of polymer forming 301.

According to other possible embodiments illustrated in FIG. 2, processes may further comprise (A) esterifying a first, FDCA-enriched fraction 251 by reaction with an esterifying agent 21, to provide an esterified FDCA-enriched fraction comprising an ester derivative of FDCA, and (B) optionally following (A), color stabilizing the esterified FDCA-enriched fraction by adding color stabilizing medium 19, to provide a stabilized, esterified FDCA-enriched fraction 221. Following (A), the processes may further comprise reacting the esterified FDCA-enriched fraction comprising an ester derivative of FDCA with a co-monomer 24 having at least two hydroxyl groups (e.g., a diol) to produce a transesterified intermediate (prepolymer) composition comprising (i) a first transesterified intermediate that is a reaction product of a mono- and/or diester derivative of FDCA and the co-monomer and being substantially free of (ii) a second transesterified intermediate that is a reaction product of an ester derivative of TPA and the co-monomer, and polymerizing the transesterified intermediate composition by polycondensation of the first transesterified intermediate to yield copolymer product 261 comprising a copolymer having furandicarboxylate moieties and being substantially free of terephthalate moieties. The steps of reacting with co-monomer 24, followed by polymerizing by polycondensation, are sub-steps of polymer forming 300. Following (B), the processes may further comprise reacting a stabilized, esterified FDCA-enriched fraction 221 with a co-monomer 24 having at least two hydroxyl groups (e.g., a diol) to produce a stabilized, transesterified intermediate (prepolymer) composition comprising (i) a first transesterified intermediate that is a reaction product of a mono- or diester derivative of FDCA and the co-monomer and being substantially free of (ii) a second transesterified intermediate that is a reaction product of an ester derivative of TPA and the co-monomer, and polymerizing the stabilized, transesterified intermediate composition by polycondensation of the first transesterified intermediate to yield a copolymer product comprising a copolymer having furandicarboxylate moieties and being substantially free of terephthalate moieties. The steps of reacting with co-monomer 24, followed by polymerizing by polycondensation are sub-steps of polymer forming 301.

According to other possible embodiments illustrated in FIG. 2, processes may further comprise (A) color stabilizing a second, TPA-enriched fraction 252 by adding color stabilizing medium 19, to provide a stabilized TPA-enriched fraction 202; and (B) optionally following (A), esterifying the stabilized TPA-enriched fraction 202 by reaction with esterifying agent 21, to provide a stabilized, esterified TPA-enriched fraction 222 comprising an ester derivative of TPA. Following (A), the processes may further comprise reacting the stabilized TPA-enriched fraction 202 with co-monomer 24 having at least two hydroxyl groups (e.g., a diol) to produce a stabilized, esterified intermediate (prepolymer)

composition comprising (i) a first esterified intermediate that is a reaction product of TPA and the co-monomer and being substantially free of (ii) a second esterified intermediate that is a reaction product of FDCA and the co-monomer, and polymerizing the stabilized, esterified intermediate composition by polycondensation of the first esterified intermediate to yield a polyester product 262 comprising a polyester having terephthalate moieties and being substantially free of furandicarboxylate moieties. The steps of reacting with co-monomer 24, followed by polymerizing by polycondensation, are sub-steps of polymer forming 302. Following (B), the processes may further comprise reacting a stabilized, esterified TPA-enriched fraction 222 comprising an ester derivative of TPA (especially the diester) with co-monomer 24 having at least two hydroxyl groups (e.g., a diol) to produce a stabilized, transesterified intermediate (prepolymer) composition comprising (i) a first transesterified intermediate that is a reaction product of a mono- and/or diester derivative of TPA and the co-monomer and being substantially free of (ii) a second transesterified intermediate that is a reaction product of an ester derivative of FDCA and the co-monomer, and polymerizing the stabilized, transesterified intermediate composition by polycondensation of the first transesterified intermediate to yield polyester product 262 comprising a polyester having terephthalate moieties and being substantially free of furandicarboxylate moieties. The steps of reacting with co-monomer 24, followed by polymerizing by polycondensation are sub-steps of polymer forming 302.

According to other possible embodiments illustrated in FIG. 2, processes may further comprise (A) esterifying a second, TPA-enriched fraction 252 by reaction with esterifying agent 21, to provide an esterified TPA-enriched fraction comprising an ester derivative of TPA, and (B) optionally following (A), color stabilizing the esterified TPA-enriched fraction by adding color stabilizing medium 19, to provide a stabilized, esterified TPA-enriched fraction 222. Following (A), the processes may further comprise reacting the esterified TPA-enriched fraction comprising an ester derivative of TPA with co-monomer 24 having at least two hydroxyl groups (e.g., a diol) to produce a transesterified intermediate (prepolymer) composition comprising (i) a first transesterified intermediate that is a reaction product of a mono- and/or diester derivative of TPA and the co-monomer and being substantially free of (ii) a second transesterified intermediate that is a reaction product of an ester derivative of FDCA and the co-monomer, and polymerizing the transesterified intermediate composition by polycondensation of the first transesterified intermediate to yield a polyester product 262 comprising a polyester having terephthalate moieties and being substantially free of furandicarboxylate moieties. The steps of reacting with co-monomer 24, followed by polymerizing by polycondensation are sub-steps of polymer forming 302. Following (B), the processes may further comprise reacting a stabilized, esterified TPA-enriched fraction 222 with co-monomer 24 having at least two hydroxyl groups (e.g., a diol) to produce a stabilized, transesterified intermediate (prepolymer) composition comprising (i) a first transesterified intermediate that is a reaction product of a mono- and/or diester derivative of TPA and the co-monomer and being substantially free of (ii) a second transesterified intermediate that is a reaction product of the ester derivative of FDCA and the co-monomer, and polymerizing the stabilized, transesterified intermediate composition by polycondensation of the first transesterified intermediate to yield polyester product 262 comprising a polyester having terephthalate moieties and being substantially free of furandicarboxylate moieties. The steps of reacting with co-monomer 24, followed by polymerizing by polycondensation are sub-steps of polymer forming 302.

FIG. 3 illustrates embodiments of the invention relating to processes for, and the resulting apparatuses/equipment obtained by, modifying (e.g., retrofitting) a monomer manufacturing facility or plant. A representative TPA production plant, for example, may have been previously constructed and may, for example, operate below its design capacity or be decommissioned altogether. The step of modifying may be used to restore overall profitability, or may improve process economics, as a result of the added ability to co-process a second monomer-forming co-feed, and especially one that is renewably-sourced, in addition to para-xylene. According to particular embodiments, a TPA production plant to be modified may comprise oxidation reactor 205 configured to receive, as feeds, (i) para-xylene, such as in para-xylene-containing feed 14, as well as (ii) oxygen, such as in oxygen-containing feed 16. The TPA production plant may further comprise a downstream TPA crystallization and recovery section 210 that is configured to separate and recycle solvent 45 from this section back to oxidation reactor 205. Modifying may comprise retrofitting the TPA production plant with a connection to an upstream carbohydrate dehydration reactor 100, for example using an existing inlet of oxidation reactor 205, such as an inlet for the para-xylene-containing feed 14, according to the dashed arrows in FIG. 3, connecting dehydration product 12 or purified portion 12' thereof (e.g., following the removal of humins) to this inlet. Otherwise, the connection may be provided with an added inlet, according to the solid arrows in FIG. 3, connecting dehydration product 12 or purified portion 12' thereof directly to oxidation reactor 205. An outlet of oxidation reactor 205 may be configured to provide (e.g., flow) oxidation effluent 18', for example comprising FDCA and TPA and/or other monomers, to the TPA crystallization and recovery section 210 that, following the retrofitting, may be configured to provide (e.g., flow) a mixed monomer composition 18 as heretofore described, having a reduced amount of solvent relative to effluent 18' or being substantially free of solvent. Modifying may further comprise configuring the TPA production plant to provide (e.g., flow or recycle) solvent 45 or at least a portion 45' thereof, back to dehydration reactor 100.

Where reference is made herein to the employment of specific transition metal salts in the metal-containing catalysts used in the process of the invention, said salts may be employed in their hydrated, semi-hydrated or non-hydrated form when forming the metal-containing catalysts. For example, when cobalt(II) acetate is used, the form of cobalt (II) acetate used in making the metal-containing catalysts used in the process of the invention may be Co(OAc)2 (non-hydrated), Co(OAc)2·xH2O (semi-hydrate), Co(OAc) 2.4H2O (hydrate). This applies likewise for other cobalt(II) salts that may be employed such as, for example, cobalt(II) bromide, cobalt(II) oxalate, and other cobalt(II) salts known to the skilled person for use in such oxidation processes. For example, the form of manganese(II) acetate used in making the metal-containing catalysts used in the process of the invention may be Mn(OAc)2 (non-hydrated), Mn(OAc) 2·xH2O (semi-hydrate), Mn(OAc)2·4H2O (hydrate). This applies likewise for other manganese(II) salts known to the skilled person for use in such oxidation processes. This applies equally for additional metal species present in the metal-containing catalysts (e.g. for cerium(III) acetate, zirconium(IV) acetate, etc.).

The following examples are set forth as representative of the present invention. These examples are illustrative and not to be construed as limiting the scope of the invention as defined in the appended claims.

EXAMPLES

Effect of Small Amounts of Co-Feeds on the Oxidation of FDCA-Forming Furanics

Experiments were performed to evaluate the effect of xylenes as co-feeds for the oxidation of FDCA-forming furanics, namely the "on path" furanics of HMF, 5-(acetoxymethyl)furfural (AcMF), and HMF dimer, representative of products obtained from the dehydration of fructose in the presence of an acetic acid and water solvent system. The dehydration product used in each experiment contained 8.5 wt-% of these compounds, in solution with this solvent system. An oxidation reactor used for the experiments was charged in each case with a homogeneous catalyst composition comprising cobalt, manganese, and bromine at concentrations of 4740 wt-ppm, 885 wt-ppm, and 1475 wt-ppm, respectively. Oxidation reaction conditions included a temperature of 180° C. and a total pressure of 15.2 bar (220 psi, 1.52 MPa), with feed rates of the dehydration product and air to the oxidation reactor being maintained at 0.9 milliliters per minute (ml/min) and 550 standard cubic centimeters per minute (sccm), for a target reaction time of 60 minutes. This target reaction time was namely a maximum time over which the reaction in each experiment was performed, with the possibility for shorter reaction times to result in cases of loss of "light off," as indicated by a drop in oxygen consumption. Following each reaction, the contents of the oxidation reactor were analyzed to determine the amounts of FDCA present, as well as amounts of FDCA-forming intermediates, such as 5-hydroxymethyl-2-furancarboxylic acid and 5-formyl-2-furancarboxylic acid, which were nonetheless valuable reaction products in terms of their ability to undergo further oxidation to form FDCA.

The specific reaction protocol employed was as follows: A 300 cm³ Ti batch reactor equipped with a gas dispersion impellor, supplied by Parr, was filled with 70 g acetic acid, 3.75 g water, 0.233 g of an HBr solution (48 wt. % HBr in water), 0.888 g Co(OAc)²·4H2O, and 0.175 g Mn(OAc)²·4H2O, then sealed and pressurized to approximately 100 psi (0.69 MPa) nitrogen before heating to 180° C. while stirring at 1200 rpm. Pressure in the reactor was maintained with a back pressure regulator (BPR) adjusted to 220 psi (1.52 MPa). Upon reaching temperature, air was flowed into the reactor at 550 standard cubic centimeters per minute (SCCM) and the effluent gas from the BPR was monitored to determine when the dry gas oxygen content of the reactor stabilized. When the oxygen stabilized, the furan feed was pumped into the reactor at 0.9 mL/min in order to initiate the reaction. Effluent oxygen was monitored throughout the run, and if oxygen consumption abruptly ceased the feed was ceased and the reaction quenched by rapidly cooling the reactor in an ice bath. Otherwise, the reaction was allowed to proceed for 60 minutes before ceasing feed and immediately quenching. After reaction, the furanic species in the liquid and solid products were analyzed by UPLC.

The furan feed used in the above procedure was prepared by slightly modifying the crude liquid product from a fructose dehydration reaction. Specifically, a mixture of 19 wt. % fructose, 0.6 wt. % glucose, 7.7 wt. % water and 2 mol % HBr (relative to total sugar) in acetic acid was fed to a continuous reactor with an internal mid-point temperature of 160° C. with a liquid residence time of 1.695 min. System pressure was maintained with a back pressure regulator at 200 psig. (1.38 MPa, gauge). The dehydration product was collected and stored prior to use as oxidation feed.

The dehydration product, prior to addition of additional solvent or co-feed, was analyzed as 4.77 wt % HMF, 3.89% wt % 5-(acetoxymethyl)furfural (AcMF), 0.15 wt % HMF dimer, 13.63% water, and 1542 ppm Br (as HBr) with the balance being acetic acid and other fructose dehydration byproducts. To prepare the furan feed for oxidation, aromatic co-feed (if present—see below), acetic acid, and water were added such that the final total on path furanics content was 8.5 wt %, the water concentration was 14.75 wt %, and the co-feed content (if present) was 1.77 wt % based on the total weight of the furan feed.

A baseline experiment was performed using a feed of the dehydration product ("furan feed") free of aromatic co-feed as described above, and three (3) separate further experiments were performed using this feed but with added amounts of the co-feeds (i) para-xylene, according to Experiment A, (ii) ortho-xylene, according to Experiment B, and (iii) mixed xylenes, according to Experiment C. The added amounts in each case represented approximately 40 mol-% of the combined FDCA-forming furanics. Compared to the baseline experiment, in which the selectivity of the converted FDCA-forming furanics to FDCA was approximately 60 mol-%, in Experiments A-C this selectivity was increased to 65-69 mol-%. Also, the total selectivity to FDCA and FDCA-forming intermediates in the baseline experiment was slightly above 80 mol-%, whereas in Experiments A-C this selectivity was increased to 84-87 mol-%. Accordingly, the addition of each of the three co-feeds resulted in an improvement in the performance of the homogeneously catalyzed oxidation of FDCA-forming furanics to FDCA.

Importantly, however, the baseline experiment was conducted for only approximately 52 minutes, at which time the reaction light off was lost and no further conversion ensued. In contrast, in Experiment B the reaction could be maintained until the target reaction time of 60 minutes, and, in Experiments A and C, light off/oxygen consumption was still proceeding even at the end of this target reaction time. Accordingly, each of the three co-feeds, and para-xylene and mixed xylenes in particular, advantageously exhibited a stabilizing effect on the oxidation of FDCA-forming furanics to FDCA.

Co-Oxidation of p-Xylene and FDCA-Forming Furanics with Co, Mn, Br Catalysts

A series of experiments was performed to further demonstrate the simultaneous oxidation of p-xylene and "on path" furanics (OPF). A solution of on path furanics was prepared by heating 218 gm of a mixture of 33 wt % corn syrup (containing 76.25 wt % fructose, 0.96 wt % dextrose, and 22.71 wt % water), enough water such that the total water content was 7.53 wt %, with 2.0 mol % HBr relative to total fructose and glucose and a balance of acetic acid to 155 deg. C. in a 300 mL titanium reactor pressurized to 220 psig (1.52 MPa, gauge) with nitrogen. Immediately after reaching 155 deg. C. the reaction was quenched in an ice bath to halt the reaction. This dehydration product was diluted with acetic acid, water, and p-xylene and used to dissolve the cobalt acetate tetrahydrate, manganese acetate tetrahydrate, and hydrobromic acid oxidation catalyst components such that the feed composition matched the targets listed in Table 1.

Oxidations were conducted in a semi-batch mode using a 300 mL Ti batch reactor equipped with a gas dispersion impellor, supplied by Parr. The reactor was initially charged with 75 gm of acetic acid, water, cobalt acetate tetrahydrate, manganese acetate tetrahydrate, and hydrobromic acid such that the feed composition matched the initial concentration targets listed in table 1. It was then sealed and pressurized to approximately 100 psi (0.69 MPa) nitrogen before heating to 180° C. while stirring at 1200 rpm. Pressure in the reactor was maintained with a back pressure regulator (BPR) adjusted to 220 psi (1.52 MPa). Upon reaching temperature, air was flowed into the reactor at 550 standard cubic centimeters per minute (SCCM) and the effluent gas from the BPR was monitored to determine when the dry gas oxygen content of the reactor stabilized. When the oxygen stabilized, the furan feed was pumped into the reactor at the specified mL/min in order to initiate the reaction. The reaction was allowed to proceed for the target run time in table 1 before ceasing feed and allowing the reaction to proceed without additional substrate for the target post-oxidation time shown in Table 1. No reactions lost light-off as described in the previous section. After reaction, the furanic species in the liquid and solid products were analyzed by UPLC. For reactions with 20% p-xylene in the feed, the furanics and p-xylene were supplied by two separate pumps with the total flow rate as shown.

reaction. Reaction products were analyzed by UPLC and total yields of on path furanics are as stated. p-Xylene appears to have little effect on the dehydration at 2 wt % and 5 wt % and perhaps has a beneficial impact at around 20 wt %.

TABLE 2

Dehydration of Fructose in P-Xylene/Acetic Acid Solvent Mixtures

| Example 10 | Reaction p-xylene content (wt %) | On Path Furanics yield (mol %) |
|---|---|---|
| 11 | 2.1 | 58.5 |
| 12 | 5.3 | 58.0 |
| 13 | 21.0 | 61.6 |

Co-Oxidation of p-Xylene and HMF with Various Catalyst Systems

A variety of catalyst systems were assessed for their ability to simultaneously oxidize HMF and p-xylene to FDCA and terephthalic acid, accordingly. All reactions were performed with 0.2 M p-xylene and 0.2 M HMF. The various

TABLE 1

Examples involving Co-Oxidation of P-Xylene and FDCA-Forming Furanics

| Examples | 1 | 2 | 3 | 4 | 5 | 6 | 7 | 8 | 9 |
|---|---|---|---|---|---|---|---|---|---|
| Feed wt % Xylene | 0.0 | 2.0 | 2.0 | 5.0 | 5.0 | 20.0 | 20.0 | 0.0 | 5.0 |
| Feed On-Path Furanics (wt %) | 8.5 | 8.5 | 8.5 | 8.5 | 8.5 | 8.5 | 8.5 | 8.5 | 8.5 |
| Feed Co (ppmw) | 2000 | 2000 | 2000 | 2000 | 2000 | 2000 | 2000 | 1000 | 1000 |
| Feed Mn (ppmw) | 600 | 600 | 600 | 600 | 600 | 600 | 600 | 300 | 300 |
| Feed Br (ppmw) | 1750 | 1750 | 1750 | 1750 | 1750 | 1750 | 1750 | 1180 | 1180 |
| Feed % H$_2$O | 15 | 15 | 15 | 15 | 15 | 15 | 15 | 15 | 15 |
| Initial Co (ppmw) | 2000 | 2000 | 2000 | 2000 | 2000 | 2000 | 2000 | 1000 | 1000 |
| Initial Mn (ppmw) | 600 | 600 | 600 | 600 | 600 | 600 | 600 | 300 | 300 |
| Initial Br (ppmw) | 1750 | 1750 | 1750 | 1750 | 1750 | 1750 | 1750 | 1180 | 1180 |
| Initial % H$_2$O | 5 | 5 | 5 | 5 | 5 | 5 | 5 | 5 | 5 |
| Feed Rate (mL/min) | 0.9 | 0.9 | 0.9 | 0.9 | 0.9 | 0.9 | 0.9 | 0.9 | 0.6 |
| Target Run Time (min) | 100 | 100 | 100 | 100 | 100 | 100 | 100 | 100 | 150 |
| Post-Oxidation (min) | 15 | 15 | 15 | 15 | 15 | 15 | 15 | 15 | 20 |
| On Path Furanics (OPF) Products (mol %) | | | | | | | | | |
| On-Path Furanics Conversion | 99.99% | 99.99% | Not Analyzed | 99.65% | Not Analyzed | 99.66% | Not Analyzed | 100.0% | 99.95% |
| Yield FDCA | 95.13% | 84.55% | | 86.43% | | 54.10% | | 80.3% | 68.56% |
| Yield Intermediates | 0.62% | 1.07% | | 1.41% | | 14.84% | | 2.0% | 3.67% |
| pX Products (mol %) | | | | | | | | | |
| pX Conversion | Not Analyzed | 100% | 100% | 99% | 100% | 99% | 99% | Not Analyzed | 100% |
| Yield TPA | | 94% | 94% | 93% | 92% | 108% | 112% | | 92% |

Production of on Path Furanics in Acetic Acid, p-Xylene, Water Solvent

The production of on path furanics in a mixture of acetic acid, p-xylene, and water was also demonstrated. Displacing some acetic acid solvent in the sugar dehydration reaction with p-xylene simplifies the integrated terephthalic acid and FDCA process and reduces acetic acid costs. In these examples, 207 g of a mixture of 33 wt % corn syrup (containing 76.25 wt % fructose, 0.96 wt % dextrose, and 22.71 wt % water), enough water such that the total water content was 7.53 wt %, 2.36 mol % HBr relative to total fructose and glucose, the specified wt % of p-xylene as in Table 2, and a balance of acetic acid to 155 deg. C. in a 300 mL titanium reactor pressurized to 220 psig (1.52 MPa, gauge) with nitrogen. Immediately after reaching 155 deg. C. the reaction was quenched in an ice bath to halt the catalysts and additives and their amounts are given in FIGS. 4 and 5, providing Tables 3 and 4. Reactions were performed in glass vials placed in a 24-well plate reactor with a shared headspace, originally provided by Freeslate. After adding all solids/liquids to the vials the reactor was sealed, pressurized to 1000 psi (6.9 MPa) of 5% oxygen in N2, then heated to 100 deg. C. for 16 hr while shaking. After cooling and depressurization, vials were dissolved in excess DMSO and analyzed for TPA and FDCA by HPLC. Reactions showing greater than 1 mol % yield of TPA or FDCA under these conditions were deemed to be confirmed as active for oxidation of p-xylene or HMF to their respective carboxylic acids. FIG. 4 depicts a Table. In the Table in FIG. 4, OAc refers to acetate, acac refers to acetylacetonate, NHPI to N-hydroxyphthalimide, and mol % is relative to the combined moles of HMF and p-xylene. FIG. 5 also depicts a Table. In the Table in FIG. 5, heterogeneous catalysts were generally purchased from Johnson Matthey and are referred to by their catalog number with the exception of Au/TiO which was provided from STREM and ground into a fine powder.

Items:

1. A process for making a mixed monomer composition comprising 2,5-furan dicarboxylic acid (FDCA) and terephthalic acid (TPA), the process comprising:

contacting an oxidation feed, in the presence of oxygen, with an oxidation catalyst to provide the mixed monomer composition, wherein the oxidation feed comprises (i) a dehydration product of one or more carbohydrates having a 6-carbon sugar unit, and (ii) para-xylene.

2. The process of item 1, wherein para-xylene represents at least 1 wt-% of a combined amount of (i) and (ii).

3. The process of any of the preceding items, wherein para-xylene represents from 1 wt-% to 75 wt. % of the combined amount of (i) and (ii).

4. The process of any of the preceding items, wherein para-xylene represents from 2 wt-% to 45 wt. % of the combined amount of (i) and (ii).

5. The process of any of the preceding items, wherein para-xylene represents from 5 wt-% to 35 wt. % of the combined amount of (i) and (ii).

6. The process of any of the preceding items, wherein said (ii) para-xylene is present in a quantity of less than 50 mol-%, preferably less than 45 mol-%, relative to 100 mol-% of said (i) dehydration product of one or more carbohydrates having a 6-carbon sugar unit.

7. The process of any of the preceding items, wherein said (ii) para-xylene is present in a quantity of from 5 mol-% to 45 mol-% relative to 100 mol-% of said (i) dehydration product of one or more carbohydrates having a 6-carbon sugar unit.

8. The process of any of the preceding items, wherein said (ii) para-xylene is present in a quantity of from 10 mol-% to 80 mol-% relative to 100 mol-% of said (i) dehydration product of one or more carbohydrates having a 6-carbon sugar unit.

9. The process of any of the preceding items, wherein said (ii) para-xylene is present in a quantity of from 30 mol-% to 60 mol-% relative to 100 mol-% of said (i) dehydration product of one or more carbohydrates having a 6-carbon sugar unit.

10. The process of any of the preceding items, wherein said (ii) para-xylene is present in a quantity of from 85 mol-% to 200 mol-% relative to 100 mol-% of said (i) dehydration product of one or more carbohydrates having a 6-carbon sugar unit.

11. The process of any of the preceding items, wherein said (ii) para-xylene is present in a quantity of from 90 mol-% to 150 mol-% relative to 100 mol-% of said (i) dehydration product of one or more carbohydrates having a 6-carbon sugar unit.

12. The process of any of the preceding items, wherein said (ii) para-xylene is present in a quantity of from 100 mol-% to 125 mol-% relative to 100 mol-% of said (i) dehydration product of one or more carbohydrates having a 6-carbon sugar unit.

13. The process of any of the preceding items, wherein said (ii) para-xylene is present in a molar quantity exceeding the molar quantity of said (i) dehydration product of one or more carbohydrates having a 6-carbon sugar unit.

14. The process of any of the preceding items, wherein (i) dehydration product of one or more carbohydrates having a 6-carbon sugar unit is present in a molar quantity exceeding the molar quantity of said (ii) para-xylene.

15. The process of any of the preceding items, wherein said one or more carbohydrates having a 6-carbon sugar unit is selected from the group consisting of starch, amylose, galactose, cellulose, hemicellulose, inulin, fructan, glucose, fructose, sucrose, maltose, cellobiose, lactose, sugar oligomers, and any combination of any thereof.

16. The process of any of the preceding items, wherein said one or more carbohydrates having a 6-carbon sugar unit is selected from hexose sugars.

17. The process of any of the preceding items, wherein said one or more carbohydrates having a 6-carbon sugar unit is fructose.

18. The process of any of the preceding items, wherein the dehydration product comprises 5-hydroxymethylfurfural (HMF) and/or an ester or ether derivative thereof.

18a. The process of any of the preceding items, wherein the dehydration product is 5-hydroxymethylfurfural (HMF) and/or an ester or ether derivative thereof.

19. The process of any of the preceding items, wherein the dehydration product comprises 5-hydroxymethylfurfural (HMF).

19a. The process of any of the preceding items, wherein the dehydration product is 5-hydroxymethylfurfural (HMF).

20. The process of any of the preceding items, wherein the dehydration product comprises an ester derivative of 5-hydroxymethylfurfural (HMF).

20a. The process of any of the preceding items, wherein the dehydration product is an ester derivative of 5-hydroxymethylfurfural (HMF).

21. The process of any of items 18, 18a, 20, or 20a, wherein said ester derivative of 5-hydroxymethylfurfural (HMF) is 5-(acetoxymethyl)furfural.

22. The process of any of the preceding items, wherein the dehydration product comprises an ether derivative of 5-hydroxymethylfurfural (HMF).

22a. The process of any of the preceding items, wherein the dehydration product is an ether derivative of 5-hydroxymethylfurfural (HMF).

23. The process of any of items 18, 18a, 22, or 22a, wherein said ether derivative of 5-hydroxymethylfurfural (HMF) is 5-(methoxymethyl)furfural.

24. The process of any of the preceding items, wherein said dehydration product of one or more carbohydrates having a 6-carbon sugar unit is made in a preceding process step, said preceding process step comprising providing a dehydration feed comprising said one or more carbohydrates having a 6-carbon sugar unit and dehydrating said one or more carbohydrates having a 6-carbon sugar unit.

25. The process of item 24, wherein said dehydration feed has a dry solids concentration from 5 wt-% to 50 wt-%, preferably from 10 wt-% to 30 wt-%.

26. The process of either of items 24 or 25, wherein said dehydration feed is an aqueous fructose solution.

27. The process of any of items 24 to 26, wherein said dehydration feed is an aqueous fructose solution comprising from 5 wt-% to 50 wt-%, preferably from 10 wt-% to 30 wt-%, fructose based on the total weight of said dehydration feed.

28. The process of item 26 or 27, wherein said fructose has a purity of at least 90 wt. %, preferably at least 97 wt. %.

29. The process of any of items 24 to 28, wherein said dehydrating step is conducted in the presence of a bromine source.

30. The process of item 29, wherein said bromine source is selected from the group consisting of hydrogen bromide, hydrobromic acid, sodium bromide, potassium bromide, molecular bromine, benzyl bromide, tetrabromoethane, 1-alkylpyridinium bromides, and 1,3-dialkylimidazolium bromides.

31. The process of any of items 29 or 30, wherein said bromine source is hydrogen bromide.

32. The process of any of items 24 to 31, wherein said dehydrating step is conducted in a solvent comprising acetic acid.

33. The process of any of items 24 to 32, wherein said dehydrating step is conducted in a solvent comprising water.

34. The process of any of 24 to 33, wherein said dehydrating step is conducted in a solvent comprising acetic acid and water.

35. The process of any of items 24 to 34, wherein said dehydrating step is conducted in a solvent comprising an alcohol.

36. The process of item 35, wherein said alcohol is selected from the group consisting of methanol, ethanol, dioxane, and combinations of any thereof.

37. The process of any of items 24 to 36, wherein said dehydrating step is conducted in a solvent comprising (ii) para-xylene.

38. The process of any of the preceding items, wherein the oxidation feed further comprises one or more humins.

39. The process of any of the preceding items, wherein the source of the oxygen with which the oxidation feed is contacted is air.

40. The process of any of the preceding items, wherein the source of the oxygen with which the oxidation feed is contacted is purified oxygen.

41. The process of any of the preceding items, wherein the oxidation catalyst is a homogenous oxidation catalyst.

42. The process of any of the preceding items, wherein the oxidation catalyst is a metal-containing catalyst.

43. The process of any of the preceding items, wherein the oxidation catalyst comprises one or more transition metals.

44. The process of any of the preceding items, wherein the oxidation catalyst comprises Co.

45. The process of any of the preceding items, wherein the oxidation catalyst comprises Mn.

46. The process of any of the preceding items, wherein the oxidation catalyst comprises Co and Mn.

47. The process according to any of the preceding items, wherein the oxidation catalyst comprises Co in the form of Co(II).

48. The process according to any of the preceding items, wherein the oxidation catalyst comprises Co in the form of cobalt(II) acetate.

49. The process according to any of the preceding items, wherein the oxidation catalyst comprises Co in the form of cobalt(II) bromide.

50. The process according to any of the preceding items, wherein the oxidation catalyst comprises Co in the form of cobalt(II) oxalate.

51. The process according to any of the preceding items, wherein the oxidation catalyst comprises Mn in the form of Mn(II).

52. The process according to any of the preceding items, wherein the oxidation catalyst comprises Mn in the form of manganese(II) acetate.

53. The process according to any of the preceding items, wherein the oxidation catalyst comprises Mn in the form of manganese(II) bromide.

54. The process according to any of the preceding items, wherein the oxidation catalyst comprises Mn in the form of manganese(II) oxalate.

55. The process of any of items 44 to 54, wherein the oxidation catalyst further comprises Zr.

56. The process of item 55, wherein said Zr is Zr(IV).

57. The process of item 56, wherein said Zr(IV) is Zr(IV) acetate.

58. The process of any of items 44 to 57, wherein the oxidation catalyst further comprises Ce.

59. The process of item 58, wherein said Ce is Ce(III).

60. The process of item 59, wherein said Ce(III) is Ce(III) acetate.

61. The process of any of items 44 to 60, wherein the oxidation catalyst further comprises Br.

62. The process of any of the preceding items, wherein the oxidation feed comprises at least one bromine-containing species.

63. The process of item 62, wherein said at least one bromine-containing species is selected from the group consisting of inorganic bromides such as HBr; metal bromides such as lithium bromide, sodium bromide, potassium bromide, magnesium bromide, calcium bromide, cobalt bromide, and manganese bromide; organic bromides such as 5-(bromomethyl) furfural and derivatives thereof, and brominated furanic oligomers; and any combination of any thereof.

64. The process of any of items 62 to 63, wherein the at least one bromine-containing species in the oxidation feed originates from the dehydration step.

65. The process of any of items 62 to 64, wherein a further bromine source in addition to the bromine-containing species present in the oxidation feed is introduced to the oxidizing step.

66. The process of item 65, wherein said further bromine source is selected from the group consisting of inorganic bromides such as HBr; metal bromides such as lithium bromide, sodium bromide, potassium bromide, magnesium bromide, calcium bromide, cobalt bromide, and manganese bromide; organic bromides such as 5-(bromomethyl) furfural and derivatives thereof, and brominated furanic oligomers; and any combination of any thereof.

67. The process of any of items 43 to 66, wherein the concentrations of the one or more transition metals in the oxidation catalyst are independently in the range from 5 wt-ppm to 10,000 wt-ppm based on the total weight of the oxidation reaction mixture.

68. The process of any of items 43 to 67, wherein the concentrations of the one or more transition metals in the oxidation catalyst are independently in the range from 10 wt-ppm to 8,000 wt-ppm based on the total weight of the oxidation reaction mixture.

69. The process of any of 43 to 68, wherein the concentrations of the one or more transition metals in the oxidation catalyst are independently in the range from 50 wt-ppm to 5,000 wt-ppm based on the total weight of the oxidation reaction mixture.

70. The process of any of the preceding items, wherein Co is present in the oxidation reaction mixture in a concentration from 10 wt-ppm to 10,000 wt-ppm based on the total weight of the oxidation reaction mixture.

71. The process of any of the preceding items, wherein Co is present in the oxidation reaction mixture in a concentration from 10 wt-ppm to 8,000 wt-ppm based on the total weight of the oxidation reaction mixture.

72. The process of any of the preceding items, wherein Co is present in the oxidation reaction mixture in a concentration from 59 wt-ppm to 5,900 wt-ppm based on the total weight of the oxidation reaction mixture.

73. The process of any of the preceding items, wherein Co is present in the oxidation reaction mixture in a concentration from 2,000 wt-ppm to 4,000 wt-ppm based on the total weight of the oxidation reaction mixture.

74. The process of any of the preceding items, wherein Mn is present in the oxidation reaction mixture in a concentration from 5 wt-ppm to 10,000 wt-ppm based on the total weight of the oxidation reaction mixture.

75. The process of any of the preceding items, wherein Mn is present in the oxidation reaction mixture in a concentration from 5 wt-ppm to 8,000 wt-ppm based on the total weight of the oxidation reaction mixture.

76. The process of any of the preceding items, wherein Mn is present in the oxidation reaction mixture in a concentration from 55 wt-ppm to 5,500 wt-ppm based on the total weight of the oxidation reaction mixture.

77. The process of any of the preceding items, wherein Mn is present in the oxidation reaction mixture in a concentration from 200 wt-ppm to 1,000 wt-ppm based on the total weight of the oxidation reaction mixture.

78. The process of any of the preceding items, wherein Br is present in the oxidation reaction mixture in a concentration from 0.1 wt-ppm to 20,000 wt-ppm based on the total weight of the oxidation reaction mixture.

79. The process of any of the preceding items, wherein Br is present in the oxidation reaction mixture in a concentration from 200 wt-ppm to 20,000 wt-ppm based on the total weight of the oxidation reaction mixture.

80. The process of any of the preceding items, wherein Br is present in the oxidation reaction mixture in a concentration from 10 wt-ppm to 10,000 wt-ppm based on the total weight of the reaction mixture.

81. The process of any of the preceding items, wherein Br is present in the oxidation reaction mixture in a concentration from 1,000 wt-ppm to 2,000 wt-ppm based on the total weight of the reaction mixture.

82. The process of any of items 78 to 81, wherein said Br is from said bromine-containing species and/or said bromine source.

83. The process of any of the preceding items, wherein the quantity of Co in the oxidation reaction mixture is from 1 to 50 mol. % relative to 100 mol. % of the (i) dehydration product of one or more carbohydrates having a 6-carbon sugar unit.

84. The process of any of the preceding items, wherein the quantity of Co in the oxidation reaction mixture is from 2 to 30 mol. % relative to 100 mol. % of the (i) dehydration product of one or more carbohydrates having a 6-carbon sugar unit.

85. The process of any of the preceding items, wherein the quantity of Co in the oxidation reaction mixture is from 10 to 20 mol. % relative to 100 mol. % of the (i) dehydration product of one or more carbohydrates having a 6-carbon sugar unit.

86. The process of any of the preceding items, wherein the molar ratio of Co:Mn in the oxidation reaction mixture is from 1:1 to 100:1.

87. The process of any of the preceding items, wherein the molar ratio of Co:Mn in the oxidation reaction mixture is from 1:1 to 10:1.

88. The process of any of the preceding items, wherein the molar ratio of Co:Mn in the oxidation reaction mixture is from 3:1 to 6:1.

89. The process of any of the preceding items, wherein the molar ratio of Br:(total metals) in the oxidation reaction mixture is from 1:100 to 10:1.

90. The process of any of the preceding items, wherein the molar ratio of Br:(total metals) in the oxidation reaction mixture is from 1:50 to 5:1.

91. The process of any of the preceding items, wherein the molar ratio of Br:(total metals) in the oxidation reaction mixture is from 1:20 to 1.5:1.

92. The process of any of the preceding items, wherein the molar ratio of Br:(total metals) in the oxidation reaction mixture is from 1:5 to 1:1.

93. The process of any of the preceding items, wherein said contacting of an oxidation feed, in the presence of oxygen, with an oxidation catalyst to provide the mixed monomer composition is conducted at a temperature from 120° C. to 250° C.

94. The process of any of the preceding items, wherein said contacting of an oxidation feed, in the presence of oxygen, with an oxidation catalyst to provide the mixed monomer composition is conducted at a temperature from 170° C. to 190° C.

95. The process of any of the preceding items, wherein the oxygen partial pressure in said contacting of an oxidation feed, in the presence of oxygen, with an oxidation catalyst to provide the mixed monomer composition is from 0.02 bar to 100 bar.

96. The process of any of the preceding items, wherein the oxygen partial pressure in said contacting of an oxidation feed, in the presence of oxygen, with an oxidation catalyst to provide the mixed monomer composition is from 0.02 bar to 21 bar.

97. The process of any of the preceding items, wherein the oxygen partial pressure in said contacting of an oxidation feed, in the presence of oxygen, with an oxidation catalyst to provide the mixed monomer composition is from 0.2 bar to 100 bar.

98. The process of any of the preceding items, wherein the oxygen partial pressure in said contacting of an oxidation feed, in the presence of oxygen, with an oxidation catalyst to provide the mixed monomer composition is from 0.2 bar to 21 bar.

99. The process of any of the preceding items, wherein the total absolute pressure in said contacting of an oxidation feed, in the presence of oxygen, with an oxidation catalyst to provide the mixed monomer composition is from 1 bar to 200 bar.

100. The process of any of the preceding items, wherein the total absolute pressure in said contacting of an oxidation feed, in the presence of oxygen, with an oxidation catalyst to provide the mixed monomer composition is from 5 bar to 100 bar.

101. The process of any of the preceding items, wherein the total absolute pressure in said contacting of an oxidation feed, in the presence of oxygen, with an oxidation catalyst to provide the mixed monomer composition is from 10 bar to 20 bar.

102. The process of any of the preceding items, wherein said contacting of the oxidation feed, in the presence of oxygen, with an oxidation catalyst is conducted in the presence of a solvent.

103. The process of item 102, wherein said solvent comprises acetic acid.

104. The process of either of items 102 or 103, wherein said solvent comprises water.

105. The process of any of items 102 to 104, wherein said solvent comprises acetic acid and water.

106. The process according to any of the preceding items, wherein said contacting of an oxidation feed, in the presence of oxygen, with an oxidation catalyst to provide the mixed monomer composition is conducted for time sufficient to produce a mixed monomer composition comprising FDCA and TPA.

107. The process according to any of the preceding items, wherein said contacting of an oxidation feed, in the presence of oxygen, with an oxidation catalyst to provide the mixed monomer composition is conducted for a period of time from 15 minutes to 24 hours.

108. The process of any one of items 1 to 107, further comprising:

(A) color stabilizing the mixed monomer composition by adding a color stabilizing medium to the mixed monomer composition, to provide a stabilized composition comprising FDCA and TPA; and (B) optionally following (A), esterifying the stabilized composition by reacting the stabilized composition with an esterifying agent, to provide a stabilized, esterified composition comprising ester derivatives of FDCA and TPA.

109. The process of item 108, wherein the esterifying agent is methanol and the ester derivatives of FDCA and TPA are respectively 2,5-furandicarboxylic acid, dimethyl ester (FDME) and dimethyl terephthalate (DMT).

110. The process of either item 108 or item 109, further comprising, either following (A):

reacting the stabilized composition comprising FDCA and TPA with a co-monomer having at least two hydroxyl groups to produce a stabilized, co-esterified intermediate composition comprising (i) a first esterified intermediate that is a reaction product of FDCA and the co-monomer and (ii) a second esterified intermediate that is a reaction product of TPA and the co-monomer, and polymerizing the stabilized, co-esterified intermediate composition by polycondensation of the first and second esterified intermediates to yield a copolymer product comprising a copolymer having furandicarboxylate moieties and terephthalate moieties, or following (B):

reacting the stabilized, esterified composition comprising the ester derivatives of FDCA and TPA with a co-monomer having at least two hydroxyl groups to produce a stabilized, co-transesterified intermediate composition comprising (i) a first transesterified intermediate that is a reaction product of the ester derivative of FDCA and the co-monomer and (ii) a second transesterified intermediate that is a reaction product of the ester derivative of TPA and the co-monomer, and polymerizing the stabilized, co-transesterified intermediate composition by polycondensation of the first and second transesterified intermediates to yield a copolymer product comprising a copolymer having furandicarboxylate moieties and terephthalate moieties.

111. The process of any one of items 1 to 107, further comprising:

(A) esterifying the mixed monomer composition by reacting the mixed monomer composition with an esterifying agent, to provide an esterified mixed monomer composition comprising ester derivatives of FDCA and TPA, and (B) optionally following (A), color stabilizing the esterified mixed monomer composition by adding a color stabilizing medium to the esterified mixed monomer composition, to provide a stabilized, esterified composition comprising ester derivatives of FDCA and TPA.

112. The process of item 111, wherein the esterifying agent is methanol and the ester derivatives of FDCA and TPA are respectively 2,5-furandicarboxylic acid, dimethyl ester (FDME) and dimethyl terephthalate (DMT).

113. The process of either item 111 or item 112, further comprising, either following (A):

separating, by distillation, the esterified mixed monomer composition into a first fraction enriched in the ester derivative of FDCA and a second fraction enriched in the ester derivative of TPA, or following (B):

separating, by distillation, the stabilized, esterified composition into a first fraction enriched in the ester derivative of FDCA and a second fraction enriched in the ester derivative of TPA.

114. The process of either item 111 or item 112, further comprising, either following (A):

reacting the esterified mixed monomer composition comprising ester derivatives of FDCA and TPA with a co-monomer having at least two hydroxyl groups to produce a co-transesterified intermediate composition comprising (i) a first transesterified intermediate that is a reaction product of the ester derivative of FDCA and the co-monomer and (ii) a second transesterified intermediate that is a reaction product of the ester derivative of TPA and the co-monomer, and polymerizing the co-transesterified intermediate composition by polycondensation of the first and second esterified intermediates to yield a copolymer product comprising a copolymer having furandicarboxylate moieties and terephthalate moieties, or following (B):

reacting the stabilized, esterified composition comprising the ester derivatives of FDCA and TPA with a co-monomer having at least two hydroxyl groups to produce a stabilized, co-transesterified intermediate composition comprising (i) a first transesterified intermediate that is a reaction product of the ester derivative of FDCA and the co-monomer and (ii) a second transesterified intermediate that is a reaction product of the ester derivative of TPA and the co-monomer, and polymerizing the stabilized, co-transesterified intermediate composition by polycondensation of the first and second transesterified intermediates to yield a copolymer product comprising a copolymer having furandicarboxylate moieties and terephthalate moieties.

115. The process of any of items 1 to 107, further comprising separating the mixed monomer composition into a first, FDCA-enriched fraction and a second, TPA-enriched fraction.

116. The process of item 115, further comprising:

(A) color stabilizing the first, FDCA-enriched fraction by adding a color stabilizing medium, to provide a stabilized FDCA-enriched fraction; and (B) optionally following (A), esterifying the stabilized FDCA-enriched fraction by reaction with an esterifying agent, to provide a stabilized, esterified FDCA-enriched fraction comprising an ester derivative of FDCA.

117. The process of item 116, wherein the esterifying agent is methanol and the ester derivative of FDCA is 2,5-furandicarboxylic acid, dimethyl ester (FDME).

118. The process of either of items 116 or 117, further comprising, either following (A):

reacting the stabilized FDCA-enriched fraction with a co-monomer having at least two hydroxyl groups to produce a stabilized, esterified intermediate composition comprising (i) a first esterified intermediate that is a reaction product of FDCA and the co-monomer and being substantially free of (ii) a second esterified intermediate that is a reaction product of TPA and the co-monomer, and polymerizing the stabilized, esterified intermediate composition by polycondensation of the first esterified intermediate to yield a copolymer product comprising a copolymer having furandicarboxylate moieties and being substantially free of terephthalate moieties, or following (B):

reacting the stabilized, esterified FDCA-enriched fraction comprising the ester derivative of FDCA with a co-monomer having at least two hydroxyl groups to produce a stabilized, transesterified intermediate composition comprising (i) a first transesterified intermediate that is a reaction product of the ester derivative of FDCA and the co-monomer and being substantially free of (ii) a second transesterified intermediate that is a reaction product of an ester derivative of TPA and the co-monomer, and polymerizing the stabilized, transesterified intermediate composition by polycondensation of the first transesterified intermediate to yield a copolymer product comprising a copolymer having furandicarboxylate moieties and being substantially free of terephthalate moieties.

119. The process of item 115, further comprising:
(A) esterifying the first, FDCA-enriched fraction by reaction with an esterifying agent, to provide an esterified FDCA-enriched fraction comprising an ester derivative of FDCA, and
(B) optionally following (A), color stabilizing the esterified FDCA-enriched fraction by adding a color stabilizing medium, to provide a stabilized, esterified FDCA-enriched fraction.

120. The process of item 119, wherein the esterifying agent is methanol and the ester derivative of FDCA is 2,5-furandicarboxylic acid, dimethyl ester (FDME).

121. The process of either of items 119 or 120, further comprising, either following (A):
reacting the esterified FDCA-enriched fraction comprising an ester derivative of FDCA with a co-monomer having at least two hydroxyl groups to produce a transesterified intermediate composition comprising (i) a first transesterified intermediate that is a reaction product of the ester derivative of FDCA and the co-monomer and being substantially free of (ii) a second transesterified intermediate that is a reaction product of an ester derivative of TPA and the co-monomer, and polymerizing the transesterified intermediate composition by polycondensation of the first transesterified intermediate to yield a copolymer product comprising a copolymer having furandicarboxylate moieties and being substantially free of terephthalate moieties, or following (B):

reacting the stabilized, esterified FDCA-enriched fraction with a co-monomer having at least two hydroxyl groups to produce a stabilized, transesterified intermediate composition comprising (i) a first transesterified intermediate that is a reaction product of the ester derivative of FDCA and the co-monomer and being substantially free of (ii) a second transesterified intermediate that is a reaction product of the ester derivative of TPA and the co-monomer, and polymerizing the stabilized, transesterified intermediate composition by polycondensation of the first transesterified intermediate to yield a copolymer product comprising a copolymer having furandicarboxylate moieties and being substantially free of terephthalate moieties.

122. The process of item 115, further comprising:
(A) color stabilizing the second, TPA-enriched fraction by adding a color stabilizing medium, to provide a stabilized TPA-enriched fraction; and
(B) optionally following (A), esterifying the stabilized TPA-enriched fraction by reaction with an esterifying agent, to provide a stabilized, esterified TPA-enriched fraction comprising an ester derivative of TPA.

123. The process of item 122, wherein the esterifying agent is methanol and the ester derivative TPA is dimethyl terephthalate (DMT).

124. The process of item 122 or item 123, further comprising, either following (A):
reacting the stabilized TPA-enriched fraction with a co-monomer having at least two hydroxyl groups to produce a stabilized, esterified intermediate composition comprising (i) a first esterified intermediate that is a reaction product of TPA and the co-monomer and being substantially free of (ii) a second esterified intermediate that is a reaction product of FDCA and the co-monomer, and polymerizing the stabilized, esterified intermediate composition by polycondensation of the first esterified intermediate to yield a copolymer product comprising a copolymer having terephthalate moieties and being substantially free of furandicarboxylate moieties, or following (B):

reacting the stabilized, esterified TPA-enriched fraction comprising the ester derivative of TPA with a co-monomer having at least two hydroxyl groups to produce a stabilized, transesterified intermediate composition comprising (i) a first transesterified intermediate that is a reaction product of the ester derivative of TPA and the co-monomer and being substantially free of (ii) a second transesterified intermediate that is a reaction product of an ester derivative of FDCA and the co-monomer, and polymerizing the stabilized, transesterified intermediate composition by polycondensation of the first transesterified intermediate to yield a copolymer product comprising a copolymer having terephthalate moieties and being substantially free of furandicarboxylate moieties.

125. The process of item 115, further comprising:
(A) esterifying the second, TPA-enriched fraction by reaction with an esterifying agent, to provide an esterified TPA-enriched fraction comprising an ester derivative of TPA, and
(B) optionally following (A), color stabilizing the esterified TPA-enriched fraction by adding a color stabilizing medium, to provide a stabilized, esterified TPA-enriched fraction.

126. The process of item 125, wherein the esterifying agent is methanol and the ester derivative TPA is dimethyl terephthalate (DMT).

127. The process of item 125 or item 126, further comprising, either following (A):
reacting the esterified TPA-enriched fraction comprising an ester derivative of TPA with a co-monomer having at least two hydroxyl groups to produce a transesterified intermediate composition comprising (i) a first transesterified intermediate that is a reaction product of the ester derivative of TPA and the co-monomer and being substantially free of (ii) a second transesterified intermediate that is a reaction product of an ester derivative of FDCA and the co-monomer, and polymerizing the transesterified intermediate composition by polycondensation of the first transesterified intermediate to yield a copolymer product comprising a copolymer having terephthalate moieties and being substantially free of furandicarboxylate moieties, or following (B):

reacting the stabilized, esterified TPA-enriched fraction with a co-monomer having at least two hydroxyl groups to produce a stabilized, transesterified intermediate composition comprising (i) a first transesterified intermediate that is a reaction product of the ester derivative of TPA and the co-monomer and being substantially free of (ii) a second transesterified intermediate that is a reaction product of the ester derivative of FDCA and the co-monomer, and polymerizing the stabilized, transesterified intermediate composition by polycondensation of the first transesterified intermediate to yield a copolymer product comprising a copolymer having terephthalate moieties and being substantially free of furandicarboxylate moieties.

128. The process of any of items 108 to 114 or 116 to 127, wherein said color stabilizing medium comprises one or more substituted phenols.

129. The process of item 128, wherein said one or more substituted phenols are selected from the group consisting of methoxy-substituted phenols (for example, butylated hydroxyanisole (BHA); 2,6-dimethoxyphenol (DMP); 2,6-di-tert-butyl-4-methoxylphenol (DTMP)), tert-butyl-substituted phenols (for example, pentaerythritol tetrakis[3-[3,5-di-tert-butyl-4-hydroxyphenyl]propionate (PETC); 2-tert-butylhydroquinone (TBHQ); ethylenebis (oxyethylene) bis-(3-(5-tert-butyl-4-hydroxy-m-tolyl)-propionate); octadecyl-3-(3,5-di-tert-butyl-4-hydroxyphenyl)-propionate), and any combination of any thereof.

130. The process of any of items 108 to 114, 116 to 127, 128 or 129, wherein said color stabilizing medium includes one or more phenyl-substituted amines (for example, 4,4'-bis($\alpha$, $\alpha$-dimethylbenzyl) diphenylamine (XDPA)), one or more phosphites (for example, tris(2,4-di-tert-butylphenyl)phosphite), antioxidant vitamins (e.g., ascorbic acid), or any combination of any thereof.

131. The process of any of items 108 to 114, 116 to 127, or 128 to 130, wherein said color stabilizing medium comprises a combination of one or more tert-butyl-substituted phenols and one or more phosphites.

132. The process of any of items 108 to 114, 116 to 127, or 128 to 131, wherein said color stabilizing medium comprises 50 wt-% PETC and 50 wt-% tris(2,4-di-tert-butylphenyl)phosphite.

133. The process of any of items 108 to 114, 116 to 127, or 128 to 131, wherein said color stabilizing medium comprises 20 wt-% octadecyl-3-(3,5-di-tert-butyl-4-hydroxy-phenyl)-propionate and 80 wt-% tris(2,4-di-tert-butylphenyl)phosphite.

134. The process of any of items 110, 114, 117, 119, 124, 127, or 128 to 133, wherein said co-monomer having at least two hydroxyl groups is a diol.

135. The process of item 134, wherein said diol is selected from the group consisting of ethylene glycol, 1,3-propanol, isomannide, isosorbide, isoidide, furan-2,5-diol, furan-2,5-dimethanol, hydroquinone, benzene-1,4-dimethanol, and any combination of any thereof.

136. The process of item 134 or 135, wherein said diol comprises isoidide.

137. The process of any of items 134 to 136, wherein said diol is isoidide

138. A process for making a mixed monomer composition comprising 2,5-furan dicarboxylic acid (FDCA) and terephthalic acid (TPA), the process comprising:

co-feeding (i) FDCA-forming furanics and (ii) para-xylene to an oxidation reactor containing an oxidation catalyst and reactant oxygen, to provide the mixed monomer composition.

139. The process of item 138, wherein para-xylene represents from 1 wt-% to 75 wt. % of the combined amount of (i) and (ii).

140. The process of any of items 138 to 139, wherein para-xylene represents from 2 wt-% to 45 wt. % of the combined amount of (i) and (ii).

141. The process of any of items 138 to 140, wherein para-xylene represents from 5 wt-% to 35 wt. % of the combined amount of (i) and (ii).

142. The process of any of items 138 to 141, wherein said (ii) para-xylene is present in a quantity of less than 50 mol-%, preferably less than 45 mol-%, relative to 100 mol-% of said (i) FDCA-forming furanics.

143. The process of any of items 138 to 142, wherein said (ii) para-xylene is present in a quantity of from 5 mol-% to 45 mol-% relative to 100 mol-% of said (i) FDCA-forming furanics.

144. The process of any of items 138 to 143, wherein said (ii) para-xylene is present in a quantity of from 10 mol-% to 80 mol-% relative to 100 mol-% of said (i) FDCA-forming furanics.

145. The process of any of items 138 to 144, wherein said (ii) para-xylene is present in a quantity of from 30 mol-% to 60 mol-% relative to 100 mol-% of said (i) FDCA-forming furanics.

146. The process of any of items 138 to 145, wherein said (ii) para-xylene is present in a quantity of from 85 mol-% to 200 mol-% relative to 100 mol-% of said (i) FDCA-forming furanics.

147. The process of any of items 138 to 146, wherein said (ii) para-xylene is present in a quantity of from 90 mol-% to 150 mol-% relative to 100 mol-% of said (i) FDCA-forming furanics.

148. The process of any of items 138 to 147, wherein said (ii) para-xylene is present in a quantity of from 100 mol-% to 125 mol-% relative to 100 mol-% of said (i) FDCA-forming furanics.

149. The process of any of items 138 to 148, wherein said (ii) para-xylene is present in a molar quantity exceeding the molar quantity of said (i) FDCA-forming furanics.

150. The process of any of items 138 to 149, wherein said (i) FDCA-forming furanics are present in a molar quantity exceeding the molar quantity of said (ii) para-xylene.

151. The process of any of items 138 to 150, wherein said (i) FDCA-forming furanics comprise 5-hydroxymethylfurfural (HMF) and/or an ester or ether derivative thereof.

152. The process of any of items 138 to 151, wherein said (i) FDCA-forming furanics comprise 5-hydroxymethylfurfural (HMF).

153. The process of any of items 138 to 152, wherein said (i) FDCA-forming furanics comprise an ester derivative of 5-hydroxymethylfurfural (HMF).

154. The process of item 153, wherein said ester derivative of 5-hydroxymethylfurfural (HMF) is 5-(acetoxymethyl) furfural.

155. The process of any of items 138 to 154, wherein said (i) FDCA-forming furanics comprise an ether derivative of 5-hydroxymethylfurfural (HMF).

156. The process of item 155, wherein said ether derivative of 5-hydroxymethylfurfural (HMF) is 5-(methoxymethyl) furfural.

157. The process of any of items 138 to 156, wherein one or more humins are also present in the oxidation reactor.

158. The process of any of items 138 to 157, wherein the source of reactant oxygen is air.

159. The process of any of items 138 to 158, wherein the source of reactant oxygen is purified oxygen.

160. The process of any of items 138 to 159, wherein the oxidation catalyst is a homogenous oxidation catalyst.

161. The process of any of items 138 to 160, wherein the oxidation catalyst is a metal-containing catalyst.

162. The process of any of items 138 to 161, wherein the oxidation catalyst comprises one or more transition metals.

163. The process of any of items 138 to 162, wherein the oxidation catalyst comprises Co.

164. The process of any of items 138 to 163, wherein the oxidation catalyst comprises Mn.

165. The process of any of items 138 to 164, wherein the oxidation catalyst comprises Co and Mn.

166. The process according to any of items 138 to 165, wherein the oxidation catalyst comprises Co in the form of Co(II).

167. The process according to any of items 138 to 166, wherein the oxidation catalyst comprises Co in the form of cobalt(II) acetate.

168. The process according to any of items 138 to 167, wherein the oxidation catalyst comprises Co in the form of cobalt(II) bromide.

169. The process according to any of items 138 to 168, wherein the oxidation catalyst comprises Co in the form of cobalt(II) oxalate.

170. The process according to any of items 138 to 169, wherein the oxidation catalyst comprises Mn in the form of Mn(II).

171. The process according to any of 138 to 170, wherein the oxidation catalyst comprises Mn in the form of manganese (II) acetate.

172. The process according to any of items 138 to 171, wherein the oxidation catalyst comprises Mn in the form of manganese(II) bromide.

173. The process according to any of items 138 to 172, wherein the oxidation catalyst comprises Mn in the form of manganese(II) oxalate.

174. The process of any of items 163 to 173, wherein the oxidation catalyst further comprises Zr.

175. The process of item 174, wherein said Zr is Zr(IV).

176. The process of item 175, wherein said Zr(IV) is Zr(IV) acetate.

177. The process of any of items 163 to 176, wherein the oxidation catalyst further comprises Ce.

178. The process of item 177, wherein said Ce is Ce(III).

179. The process of item 178, wherein said Ce(III) is Ce(III) acetate.

180. The process of any of items 138 to 179, wherein the oxidation catalyst further comprises Br.

181. The process according to any of items 138 to 180, wherein a bromine source is fed to the oxidation reactor.

182. The process according to item 181, wherein said bromine source is selected from the group consisting of inorganic bromides such as HBr; metal bromides such as lithium bromide, sodium bromide, potassium bromide, magnesium bromide, calcium bromide, cobalt bromide, and manganese bromide; organic bromides such as 5-(bromomethyl) furfural and derivatives thereof, and brominated furanic oligomers; and any combination of any thereof.

183. The process of any of items 162 to 182, wherein the concentrations of the one or more transition metals in the oxidation catalyst are independently in the range from 5 wt-ppm to 10,000 wt-ppm based on the total weight of the oxidation reaction mixture.

184. The process of any of items 162 to 183, wherein the concentrations of the one or more transition metals in the oxidation catalyst are independently in the range from 10 wt-ppm to 8,000 wt-ppm based on the total weight of the oxidation reaction mixture.

185. The process of any of items 162 to 184, wherein the concentrations of the one or more transition metals in the oxidation catalyst are independently in the range from 50 wt-ppm to 5,000 wt-ppm based on the total weight of the oxidation reaction mixture.

186. The process of any of items 138 to 185, wherein Co is present in the oxidation reaction mixture in a concentration from 10 wt-ppm to 10,000 wt-ppm based on the total weight of the oxidation reaction mixture.

187. The process of any of items 138 to 186, wherein Co is present in the oxidation reaction mixture in a concentration from 10 wt-ppm to 8,000 wt-ppm based on the total weight of the oxidation reaction mixture.

188. The process of any of items 138 to 187, wherein Co is present in the oxidation reaction mixture in a concentration from 59 wt-ppm to 5,900 wt-ppm based on the total weight of the oxidation reaction mixture.

189. The process of any of items 138 to 188, wherein Co is present in the oxidation reaction mixture in a concentration from 2,000 wt-ppm to 4,000 wt-ppm based on the total weight of the oxidation reaction mixture.

190. The process of any of items 138 to 189, wherein Mn is present in the oxidation reaction mixture in a concentration from 5 wt-ppm to 10,000 wt-ppm based on the total weight of the oxidation reaction mixture.

191. The process of any of items 138 to 190, wherein Mn is present in the oxidation reaction mixture in a concentration from 5 wt-ppm to 8,000 wt-ppm based on the total weight of the oxidation reaction mixture.

192. The process of any of items 138 to 191, wherein Mn is present in the oxidation reaction mixture in a concentration from 55 wt-ppm to 5,500 wt-ppm based on the total weight of the oxidation reaction mixture.

193. The process of any of items 138 to 192, wherein Mn is present in the oxidation reaction mixture in a concentration from 200 wt-ppm to 1,000 wt-ppm based on the total weight of the oxidation reaction mixture.

194. The process of any of items 138 to 193, wherein Br is present in the oxidation reaction mixture in a concentration from 0.1 wt-ppm to 20,000 wt-ppm based on the total weight of the oxidation reaction mixture.

195. The process of any of items 138 to 194, wherein Br is present in the oxidation reaction mixture in a concentration from 200 wt-ppm to 20,000 wt-ppm based on the total weight of the oxidation reaction mixture.

196. The process of any of items 138 to 195, wherein Br is present in the oxidation reaction mixture in a concentration from 10 wt-ppm to 10,000 wt-ppm based on the total weight of the reaction mixture.

197. The process of any of items 138 to 196, wherein Br is present in the oxidation reaction mixture in a concentration from 1,000 wt-ppm to 2,000 wt-ppm based on the total weight of the reaction mixture.

198. The process of any of items 138 to 197, wherein the quantity of Co in the oxidation reaction mixture is from 1 to 50 mol. % relative to 100 mol. % of the (i) FDCA-forming furanics.

199. The process of any of items 138 to 198, wherein the quantity of Co in the oxidation reaction mixture is from 2 to 30 mol. % relative to 100 mol. % of the (i) FDCA-forming furanics.

200. The process of any of items 138 to 199, wherein the quantity of Co in the oxidation reaction mixture is from 10 to 20 mol. % relative to 100 mol. % of the (i) FDCA-forming furanics.

201. The process of any of items 138 to 200, wherein the quantity of Co in the oxidation reaction mixture is from 1 to 50 mol. % relative to 100 mol. % of the (i) FDCA-forming furanics.

202. The process of any of items 138 to 201, wherein the molar ratio of Co:Mn in the oxidation reaction mixture is from 1:1 to 100:1.

203. The process of any of items 138 to 202, wherein the molar ratio of Co:Mn in the oxidation reaction mixture is from 1:1 to 10:1.

204. The process of any of items 138 to 203, wherein the molar ratio of Co:Mn in the oxidation reaction mixture is from 3:1 to 6:1.

205. The process of any of items 138 to 204, wherein the molar ratio of Br:(total metals) in the oxidation reaction mixture is from 1:100 to 10:1.

206. The process of any of items 138 to 205, wherein the molar ratio of Br:(total metals) in the oxidation reaction mixture is from 1:50 to 5:1.

207. The process of any of items 138 to 206, wherein the molar ratio of Br:(total metals) in the oxidation reaction mixture is from 1:20 to 1.5:1.

208. The process of any of items 138 to 207, wherein the molar ratio of Br:(total metals) in the oxidation reaction mixture is from 1:5 to 1:1.

209. The process of any of items 138 to 208, wherein the oxidation reactor is operated under oxidation conditions including a temperature from 120° C. to 250° C.

210. The process of any of items 138 to 209, wherein the oxidation reactor is operated under oxidation conditions including a temperature from 170° C. to 190° C.

211. The process of any of items 138 to 210, wherein the oxidation reactor is operated under oxidation conditions including an oxygen partial pressure from 0.02 bar to 100 bar.

212. The process of any of items 138 to 211, wherein the oxidation reactor is operated under oxidation conditions including an oxygen partial pressure from 0.02 bar to 21 bar.

213. The process of any of items 138 to 212, wherein the oxidation reactor is operated under oxidation conditions including an oxygen partial pressure from 0.2 bar to 100 bar.

214. The process of any of items 138 to 213, wherein the oxidation reactor is operated under oxidation conditions including an oxygen partial pressure from 0.2 bar to 21 bar.

215. The process of any of items 138 to 214, wherein the oxidation reactor is operated under oxidation conditions including a total absolute pressure from 1 bar to 200 bar.

216. The process of any of items 138 to 215, wherein the oxidation reactor is operated under oxidation conditions including a total absolute pressure from 5 bar to 100 bar.

217. The process of any of items 138 to 216, wherein the oxidation reactor is operated under oxidation conditions including a total absolute pressure from 10 bar to 20 bar.

218. The process of any of items 138 to 217, wherein said oxidation reactor further contains a solvent.

219. The process of item 218, wherein said solvent comprises acetic acid.

220. The process of item 218 or item 219, wherein said solvent comprises water.

221. The process of any of items 218 to 220, wherein said solvent comprises acetic acid and water.

222. The process according to any of items 138 to 221, wherein the oxidation reactor is operated under oxidation conditions for a time sufficient to produce a mixed monomer composition comprising FDCA and TPA.

223. The process according to any of items 138 to 222, wherein the oxidation reactor is operated under oxidation conditions for a period of time from 15 minutes to 24 hours.

224. The process of any of items 138 to 223, wherein the mixed monomer composition comprises, as color-forming byproducts, an aldehyde derivative of FDCA and an aldehyde derivative of TPA,
   the process further comprising selectively hydrogenating one or both of the aldehyde derivative of FDCA and the aldehyde derivative of TPA.

225. The process of item 224, wherein the aldehyde derivative of FDCA is 5-formyl-2-furancarboxylic acid (FFCA) and the aldehyde derivative of TPA is 4-carboxybenzaldehyde (4-CBA).

226. The process of either item 224 or item 225, wherein said selectively hydrogenating one or both of the aldehyde derivative of FDCA and the aldehyde derivative of TPA occurs following a separation of the mixed monomer composition into an FDCA-enriched fraction and a TPA-enriched fraction.

227. The process of any of items 138 to 223, wherein the mixed monomer composition comprises, as color-forming byproducts, an aldehyde derivative of FDCA and an aldehyde derivative of TPA,
   the process further comprising, in a step of esterifying one or both of the FDCA and TPA, producing, as further color-forming byproducts, one or both of an aldehyde derivative of an ester derivative of FDCA and an aldehyde derivative of an ester derivative of TPA, and
   the process further comprising selectively hydrogenating one or both of the aldehyde derivative of the ester derivative of FDCA and the aldehyde derivative of the ester derivative of TPA.

228. The process of item 227, wherein the aldehyde derivative of the ester derivative of FDCA is 5-formyl-2-furancarboxylic acid methyl ester (FFME) and the aldehyde derivative of the ester derivative of TPA is 4-carboxybenzaldehyde methyl ester (4-CME).

229. The process of either item 227 or item 228, wherein the process comprises esterifying both of the FDCA and TPA, in a step of esterifying the mixed monomer composition by reacting the mixed monomer composition with an esterifying agent, to provide an esterified mixed monomer composition comprising both the aldehyde derivative of the ester derivative of FDCA and the aldehyde derivative of the ester derivative of TPA.

230. The process of item 229, wherein the esterifying both of the FDCA and TPA occurs upstream of a separation of the esterified mixed monomer composition into first fraction enriched in an ester derivative of FDCA and a second fraction enriched in an ester derivative of TPA.

231. The process of item 228, wherein the esterifying one or both of the FDCA and TPA occurs in a step of esterifying one or both of an FDCA-enriched fraction and a TPA-enriched fraction, by reaction with an esterifying agent, downstream of a separation of the mixed monomer composition into the FDCA-enriched fraction and the TPA-enriched fraction.

232. The process of any of items 224 to 231, wherein said selective hydrogenation step comprises contacting said mixed monomer composition with hydrogen in the presence of a hydrogenation catalyst.

233. The process of item 232, wherein said hydrogenation catalyst comprises Pt, Ru, and Sn.

234. The process of any of items 138 to 233, wherein the co-feeding comprises providing the FDCA-forming furanics and the para-xylene as separate feed streams to the oxidation reactor.

235. The process of any of items 138 to 233, wherein the co-feeding comprises combining the FDCA-forming furanics and the para-xylene into a combined feed stream and providing the combined feed stream to the oxidation reactor.

236. The process of any of items 138 to 233, further comprising, prior to said co-feeding, dehydrating one or more carbohydrates to obtain the FDCA-forming furanics.

237. The process of item 236, wherein said dehydrating step is conducted in the presence of a bromine source.

238. The process of item 237, wherein said bromine source is selected from the group consisting of hydrogen bromide, hydrobromic acid, sodium bromide, potassium bromide, molecular bromine, benzyl bromide, tetrabromoethane, 1-alkylpyridinium bromides, and 1,3-dialkylimidazolium bromides.

239. The process of any of items 237 or 238, wherein said bromine source is hydrogen bromide.

240. The process of any of items 237 or 238, wherein said bromine source is hydrobromic acid.

241. The process of any of items 236 to 240, wherein said dehydrating is performed with said one or more carbohydrates in a solution comprising a lower carboxylic acid or a lower alcohol.

242. The process of item 241, wherein said lower carboxylic acid is acetic acid.

243. The process of item 241 or item 242, wherein said alcohol is selected from the group consisting of methanol, ethanol, and combinations of any thereof.

244. The process of any of items 241 to 243, wherein the solution further comprises para-xylene.

245. The process of item 244, wherein at least a portion of the para-xylene used in the dehydrating step is unconverted para-xylene recovered from the mixed monomer composition following the oxidation step and recycled back to the dehydrating step.

246. The process of any of items 236 to 245, wherein the dehydrating is performed with said one or more carbohydrates in a solution comprising para-xylene and in the presence of an acid for catalyzing the dehydration.

247. The process of item 246, wherein said acid for catalyzing the dehydration is other than said lower carboxylic acid.

248. The process of either of items 246 or 247, wherein said acid for catalyzing the dehydration is hydrobromic acid.

249. The process of item 246, wherein at least a portion of the para-xylene used in the dehydrating step is unconverted para-xylene recovered from the mixed monomer composition following the oxidation step and recycled back to the dehydrating step.

250. The process of any of items 236 to 249, wherein the oxidation catalyst comprises Co, Mn and Br, and further wherein at least a portion of the Br is recovered, recycled and supplied to the dehydrating step.

251. The process of item 250, wherein at least a portion of the Br supplied to the dehydrating step is in the form of hydrogen bromide.

252. The process of item 251, wherein, after said dehydrating and before said co-feeding, a humin content of said FDCA-forming furanics is not reduced.

253. The process of item 236, wherein, after said dehydrating and before said co-feeding, a humin content of said FDCA-forming furanics is not reduced.

254. The process of any of items 236 to 253, wherein the one or more carbohydrates are selected from hexose sugars.

255. The process of any of items 236 to 254, wherein said one or more carbohydrates is fructose.

256. The process of any of items 236 to 255, wherein said one or more carbohydrates is an aqueous fructose solution.

257. The process of any of items 236 to 256, wherein said one or more carbohydrates is an aqueous fructose solution comprising from 5 wt-% to 50 wt-%, preferably from 10 wt-% to 30 wt-%, fructose based on the total weight of the solution.

258. The process of any of items 255 to 257, wherein said fructose has a purity of at least 90 wt. %, preferably at least 97 wt. %.

259. A method for modifying a terephthalic acid (TPA) production plant, said production plant comprising an oxidation reactor adapted to receive para-xylene and oxygen as feeds, and further comprising a downstream TPA crystallization and recovery section configured to separate solvent from TPA and recycle the solvent to the oxidation reactor, the method comprising retrofitting said TPA production plant with a connection from an existing inlet of the oxidation reactor, or from an added inlet of the oxidation reactor, to an upstream carbohydrate dehydration reactor.

The invention claimed is:

1. A process for making a mixed monomer composition comprising 2,5-furan dicarboxylic acid (FDCA) and terephthalic acid (TPA), the process comprising:

co-feeding (i) FDCA-forming furanics and (ii) para-xylene to an oxidation reactor containing an oxidation catalyst and reactant oxygen, to provide the mixed monomer composition; wherein Said oxidation catalyst comprises either or both of Co and Mn.

2. The process of claim 1, wherein the mixed monomer composition comprises an aldehyde derivative of FDCA and an aldehyde derivative of TPA, and the process further comprises selectively hydrogenating one or both of the aldehyde derivative of FDCA and the aldehyde derivative of TPA.

3. The process of claim 2, wherein said selectively hydrogenating one or both of the aldehyde derivative of FDCA and the aldehyde derivative of TPA occurs following a separation of the mixed monomer composition into an FDCA-enriched fraction and a TPA-enriched fraction.

4. The process of claim 1, wherein the mixed monomer composition comprises an aldehyde derivative of FDCA and an aldehyde derivative of TPA, the process further comprises, in a step of esterifying one or both of the FDCA and TPA, producing one or both of an aldehyde derivative of an ester derivative of FDCA and an aldehyde derivative of an ester derivative of TPA, and the process further comprises selectively hydrogenating one or both of the aldehyde derivative of the ester derivative of FDCA and the aldehyde derivative of the ester derivative of TPA.

5. The process of claim 4, wherein the process comprises esterifying both of the FDCA and TPA by reacting the mixed monomer composition with an esterifying agent, to provide an esterified mixed monomer composition comprising both the aldehyde derivative of the ester derivative of FDCA and the aldehyde derivative of the ester derivative of TPA.

6. The process of claim 4, wherein the esterifying one or both of the FDCA and TPA occurs in a step of esterifying one or both of an FDCA-enriched fraction and a TPA-enriched fraction, by reaction with an esterifying agent, downstream of a separation of the mixed monomer composition into the FDCA-enriched fraction and the TPA-enriched fraction.

7. The process of claim 1, wherein the co-feeding comprises providing the FDCA-forming furanics and the para-xylene as separate feed streams to the oxidation reactor.

8. The process of claim 1, wherein the co-feeding comprises combining the FDCA-forming furanics and the para-xylene into a combined feed stream and providing the combined feed stream to the oxidation reactor.

9. The process of claim 1, further comprising, prior to said co-feeding, dehydrating one or more carbohydrates in a solution comprising a lower carboxylic acid or a lower alcohol to obtain the FDCA-forming furanics in a crude dehydration product mixture, and supplying the FDCA-forming furanics directly to the oxidation reactor with the para-xylene in a separate feed stream or in a combined feed stream.

10. The process of claim 9, wherein the solution further comprises para-xylene.

* * * * *